(12) United States Patent
Shu

(10) Patent No.: US 10,188,778 B2
(45) Date of Patent: Jan. 29, 2019

(54) ARTIFICIAL HEART

(71) Applicant: Stephen K. Shu, Irvine, CA (US)

(72) Inventor: Stephen K. Shu, Irvine, CA (US)

(73) Assignee: Stephen K. Shu, Irvine, CA (US)

( * ) Notice: Subject to any disclaimer, the term of this patent is extended or adjusted under 35 U.S.C. 154(b) by 0 days.

(21) Appl. No.: 15/191,289

(22) Filed: Jun. 23, 2016

(65) Prior Publication Data
US 2018/0353666 A1    Dec. 13, 2018

(51) Int. Cl.
*A61M 1/10*    (2006.01)
*A61M 1/12*    (2006.01)

(52) U.S. Cl.
CPC ........ *A61M 1/1055* (2014.02); *A61M 1/1087* (2014.02); *A61M 1/12* (2013.01); *A61M 1/1005* (2014.02); *A61M 1/1048* (2014.02); *A61M 2205/3523* (2013.01); *A61M 2205/50* (2013.01); *A61M 2205/82* (2013.01); *A61M 2205/8206* (2013.01); *A61M 2205/8281* (2013.01); *A61M 2205/8287* (2013.01); *A61M 2210/125* (2013.01)

(58) Field of Classification Search
CPC .................................................. A61M 1/1055
See application file for complete search history.

(56) References Cited

U.S. PATENT DOCUMENTS

| | | |
|---|---|---|
| 1,737,710 A | 6/1927 | Erbach |
| 3,613,677 A | 10/1971 | Blasko |
| 4,375,941 A | 3/1983 | Child |
| 4,611,578 A | 9/1986 | Heimes |
| 4,648,877 A | 3/1987 | Lundback |
| 4,786,240 A | 11/1988 | Koroly et al. |
| 5,241,986 A | 9/1993 | Yie |
| 5,411,552 A | 5/1995 | Andersen et al. |
| 5,758,666 A | 6/1998 | Larson, Jr. et al. |
| 5,766,207 A | 6/1998 | Potter et al. |
| 7,575,594 B2 | 8/2009 | Sieracki |
| RE41,394 E | 6/2010 | Bugge et al. |
| 8,021,422 B2 | 9/2011 | Tinker |
| 8,419,789 B2 | 4/2013 | Shu et al. |
| 9,242,033 B2 | 1/2016 | Shu et al. |
| 2010/0057046 A1 | 3/2010 | Stevens et al. |
| 2011/0144744 A1 | 6/2011 | Wampler |
| 2013/0041460 A1 | 2/2013 | Heilman et al. |
| 2016/0213469 A1 | 7/2016 | Shu et al. |

OTHER PUBLICATIONS

U.S. Appl. No. 15/005,706, filed Jan. 25, 2016, Shu et al.

*Primary Examiner* — Jacqueline Woznicki
(74) *Attorney, Agent, or Firm* — Knobbe, Martens, Olson & Bear, LLP

(57) ABSTRACT

Disclosed herein is a fully implantable artificial heart. The use of flat helical springs to align and reciprocate a bellows structure allows the bellows to pump blood, the multiple solenoids with floating magnetized rods and permanent magnet assemblies held by the flat helical springs provide the power. The artificial heart pumps blood with virtually no friction and no parts to wear out. The use of solenoids advantageously move blood in a gentle, controllable manner.

14 Claims, 29 Drawing Sheets

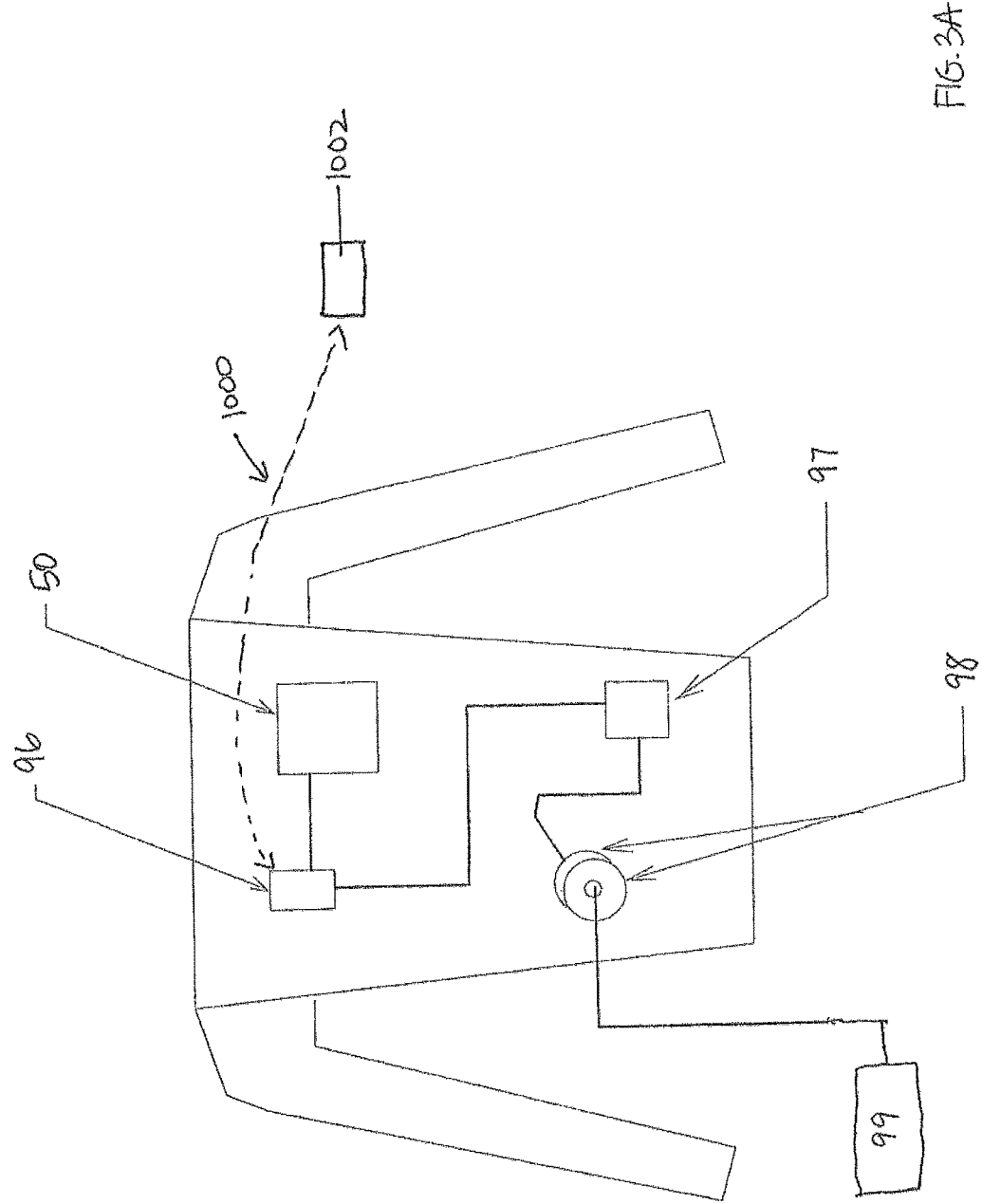

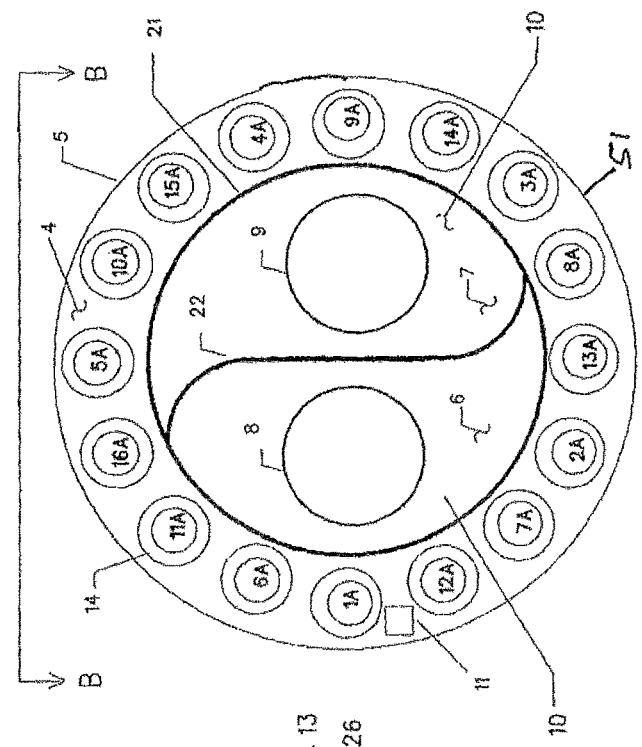
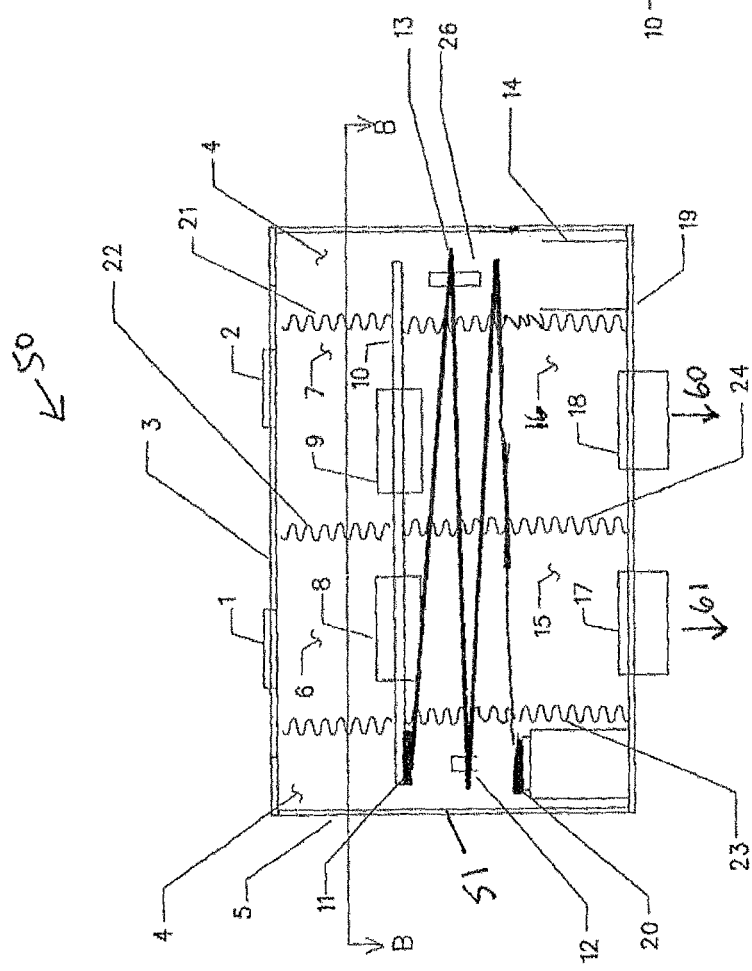
FIG. 4A
FIG. 4B

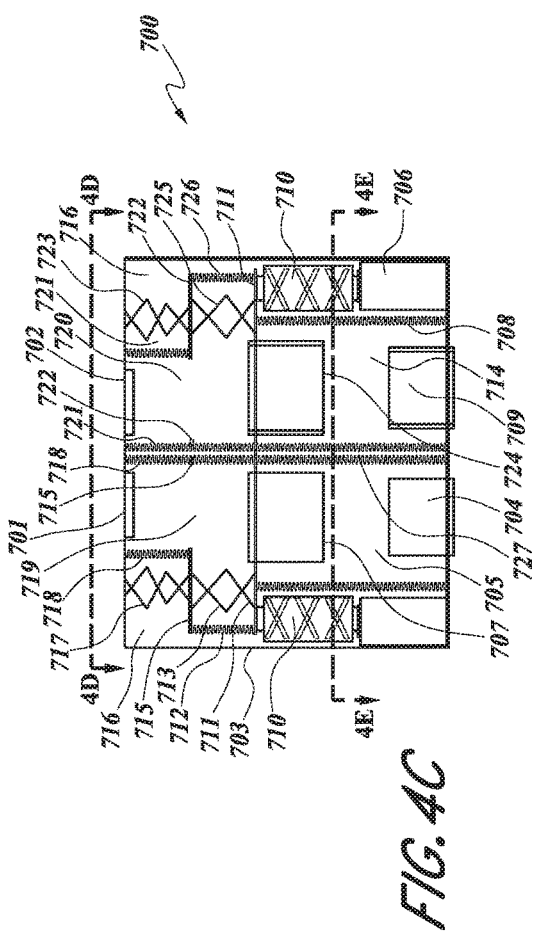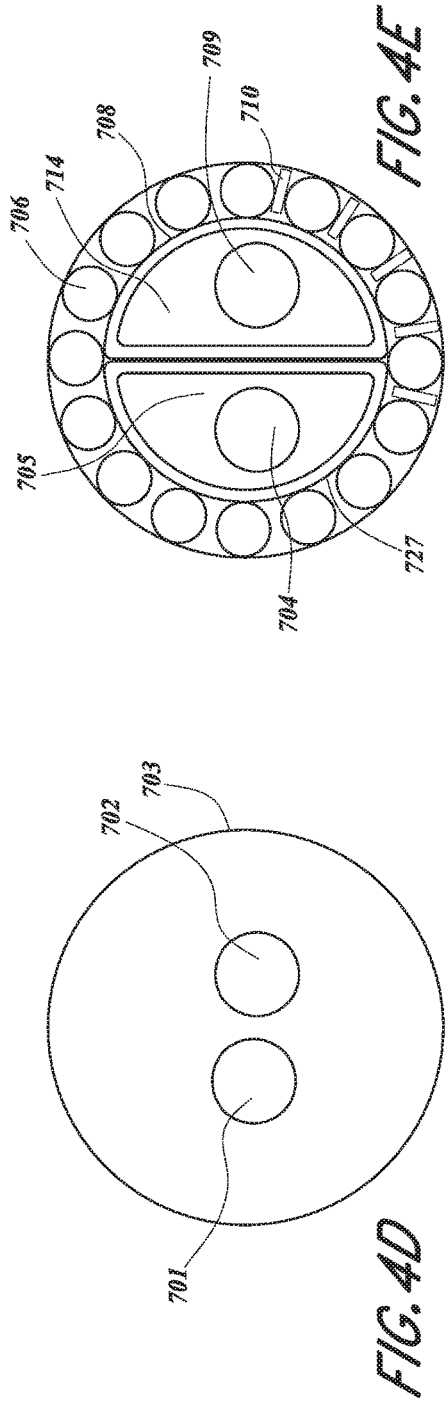

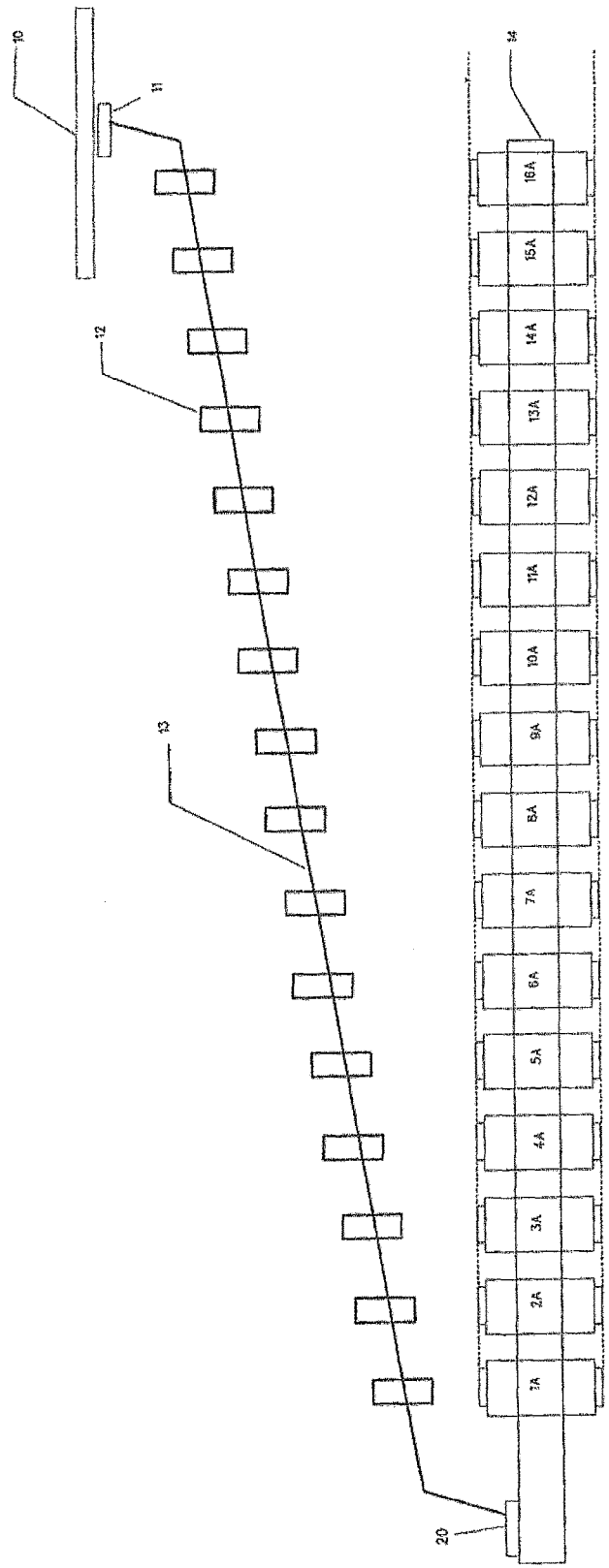

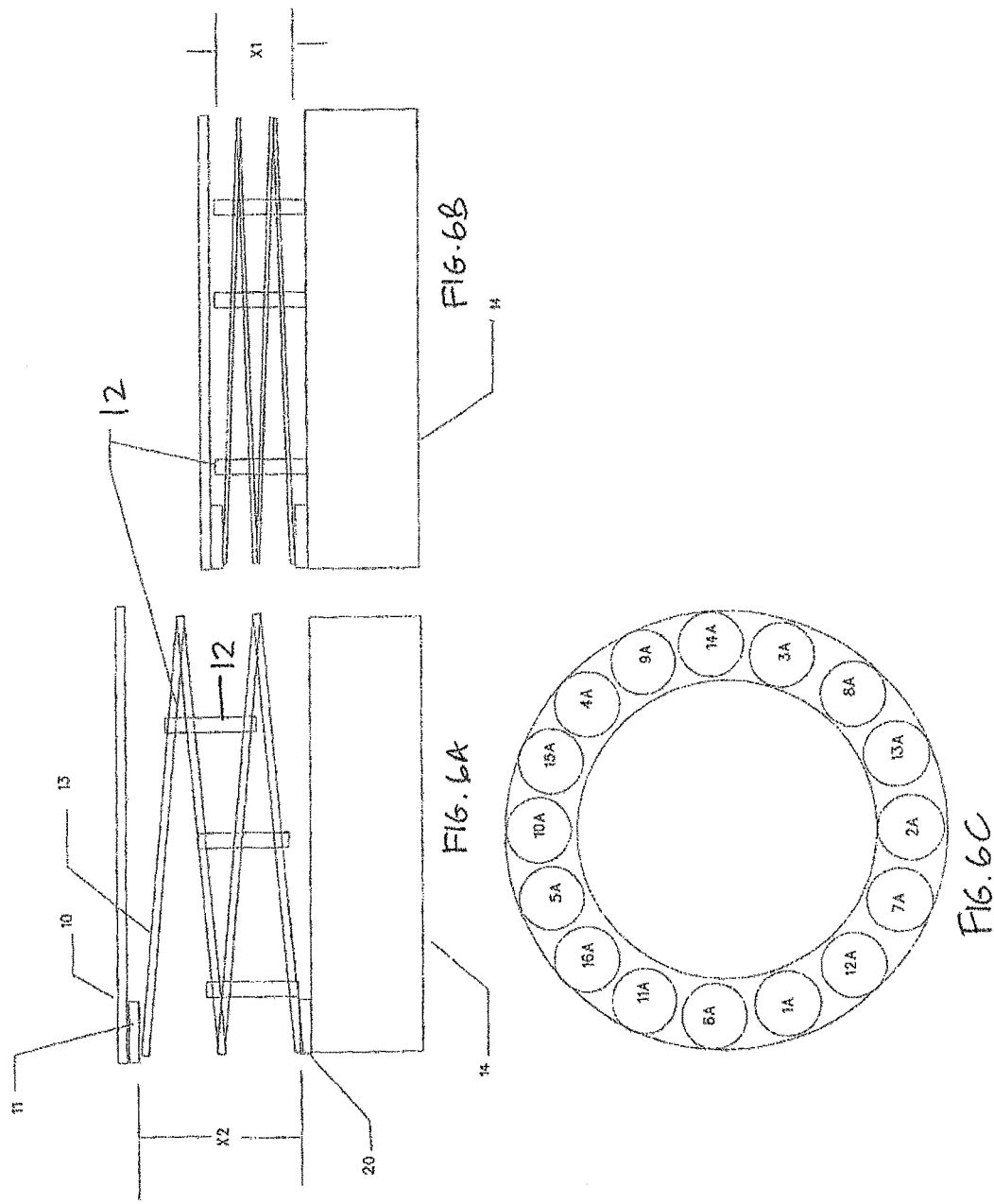

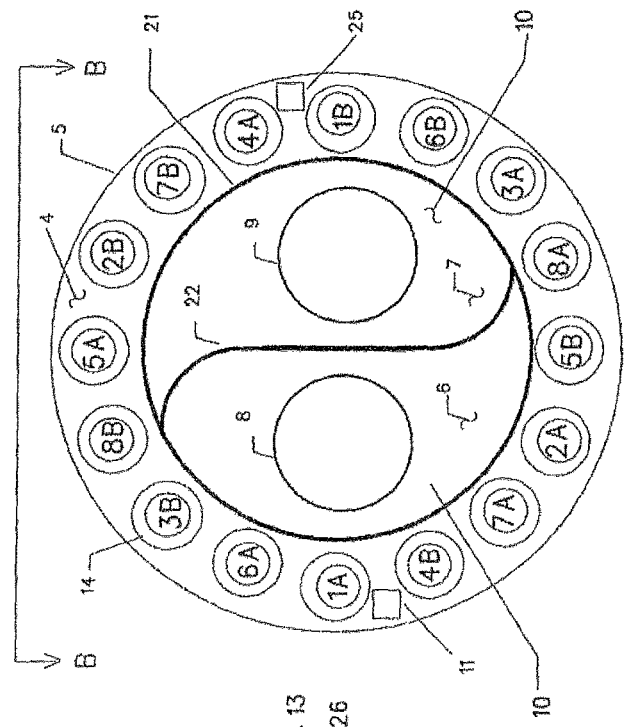
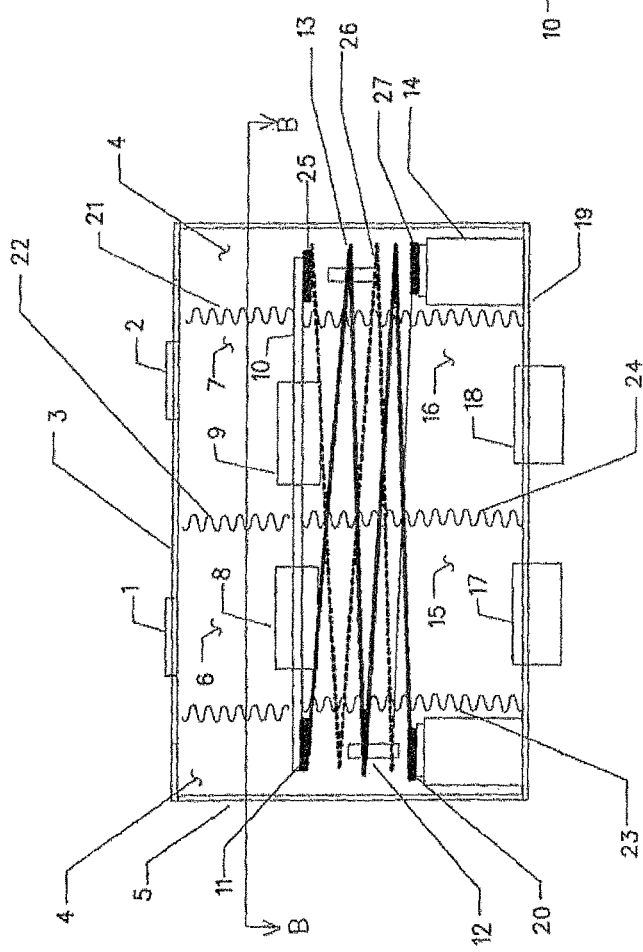

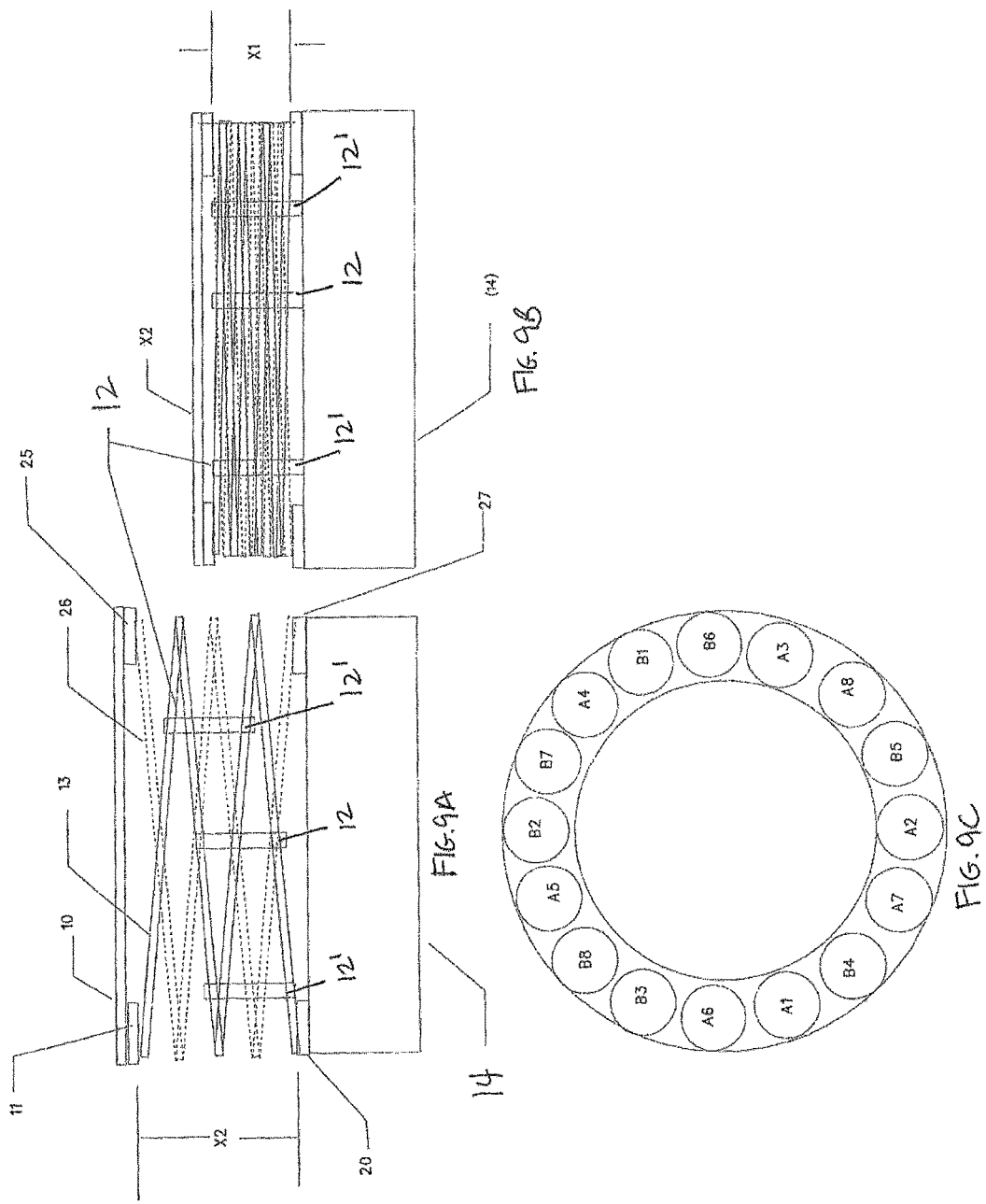

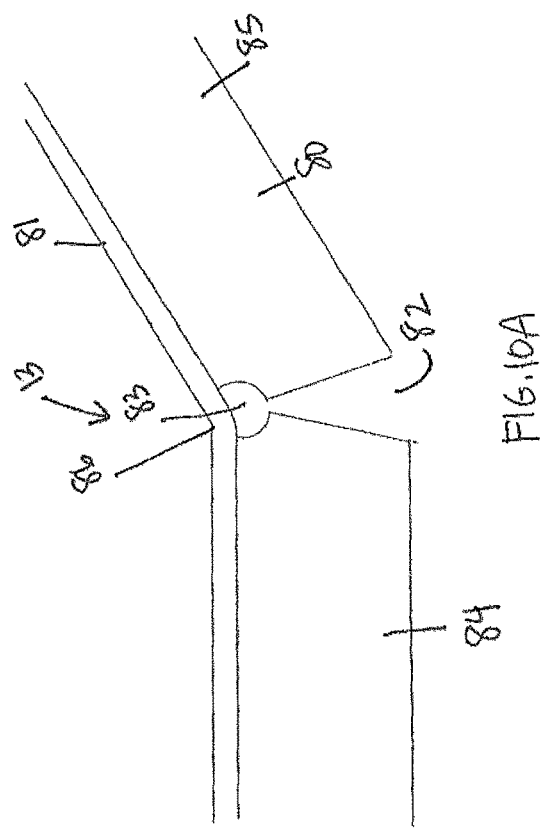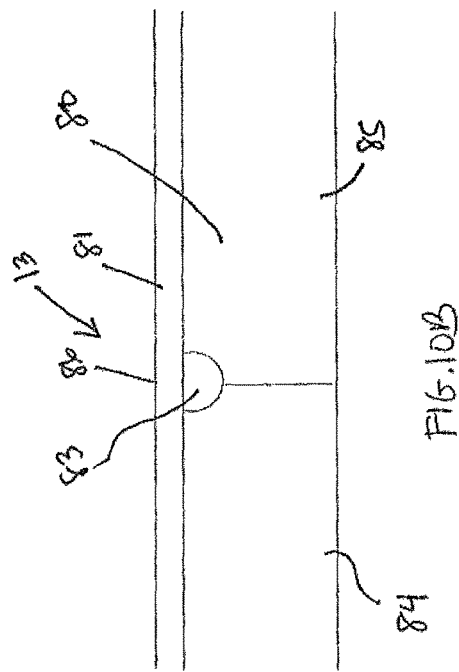

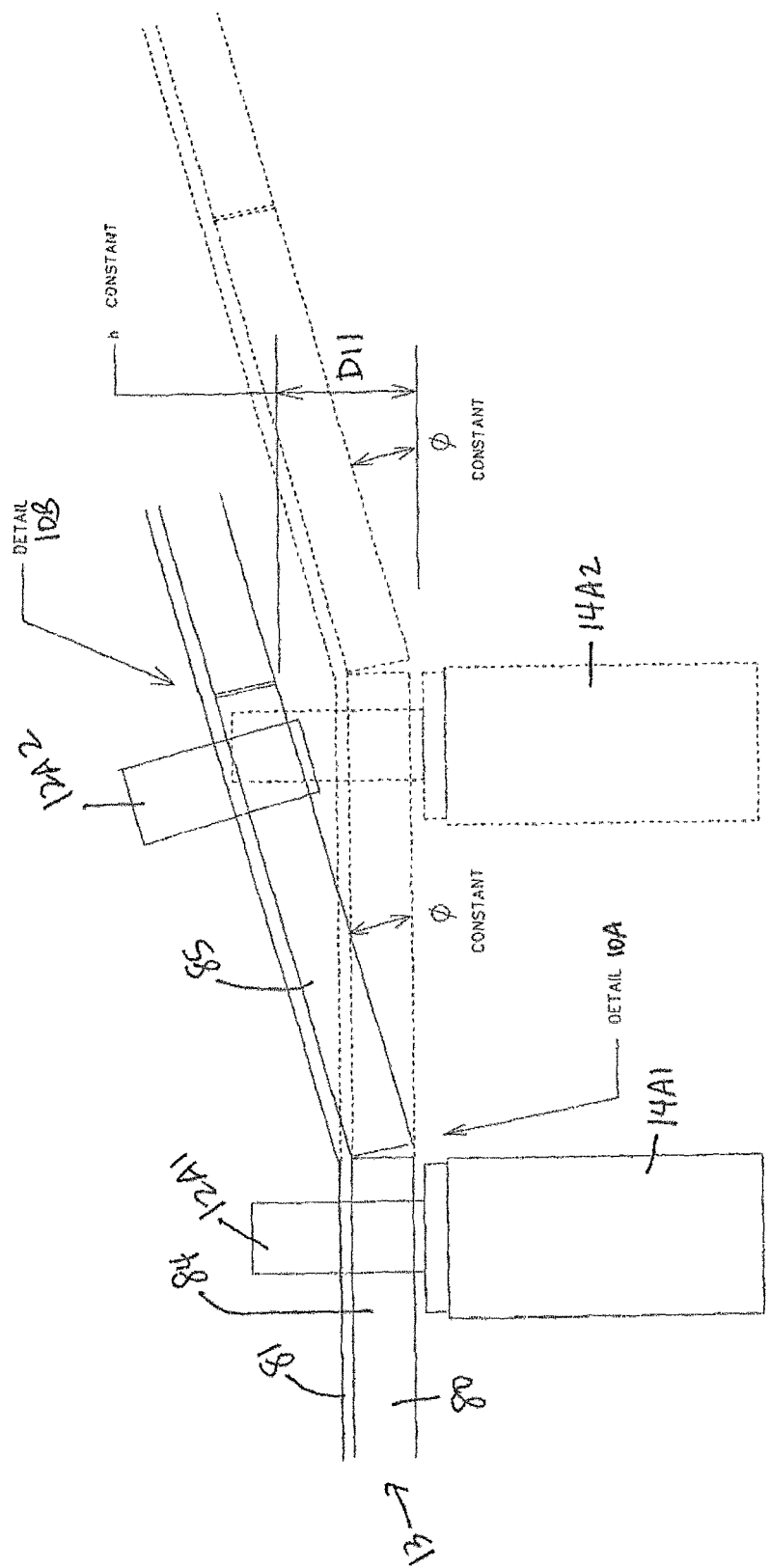

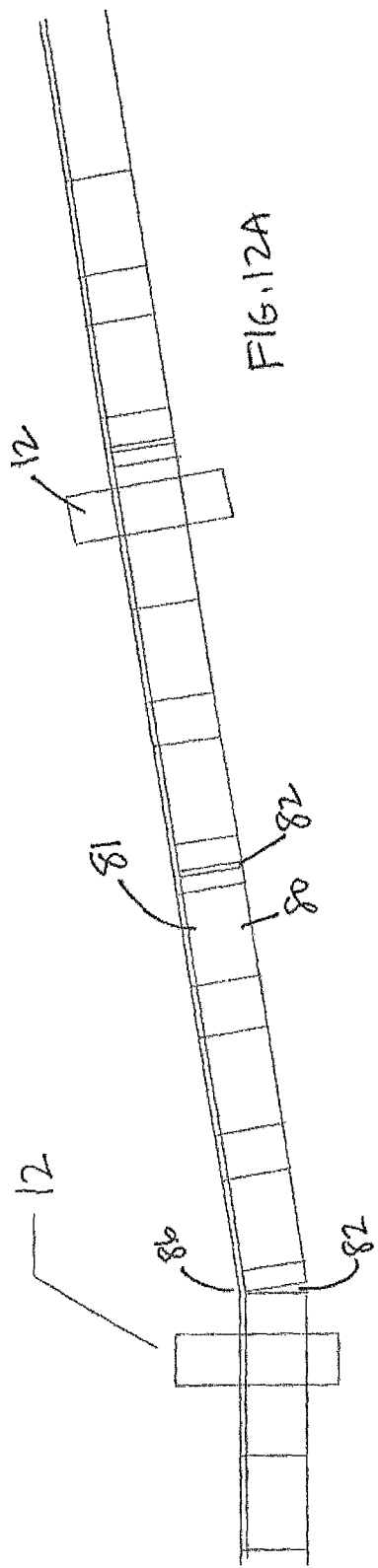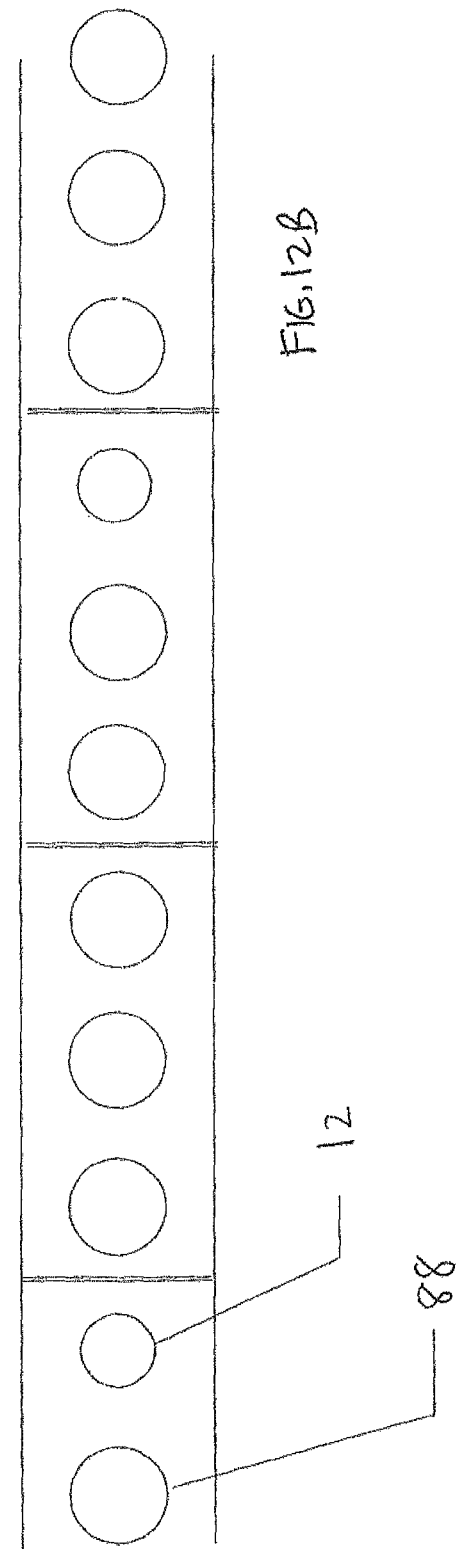

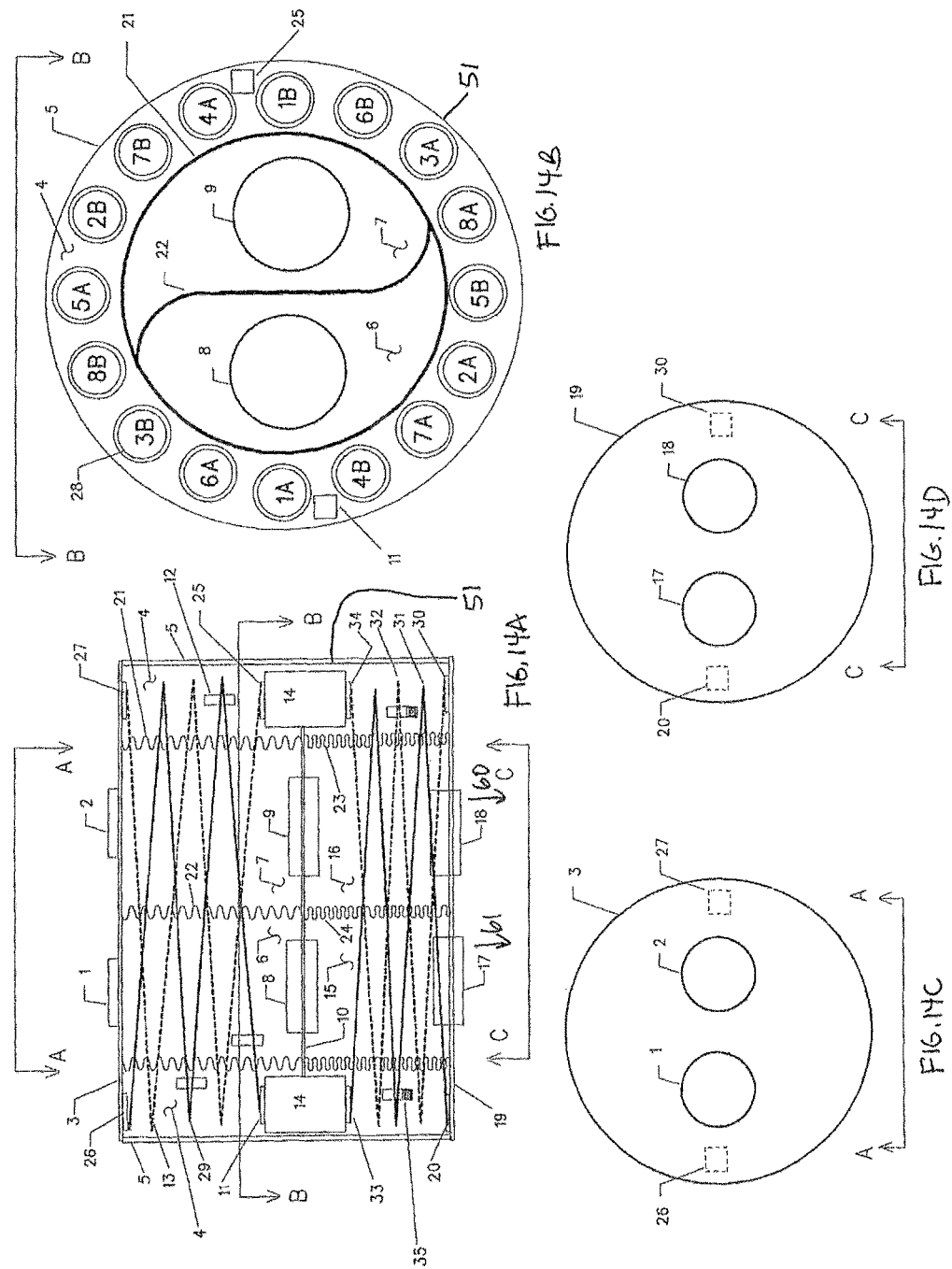

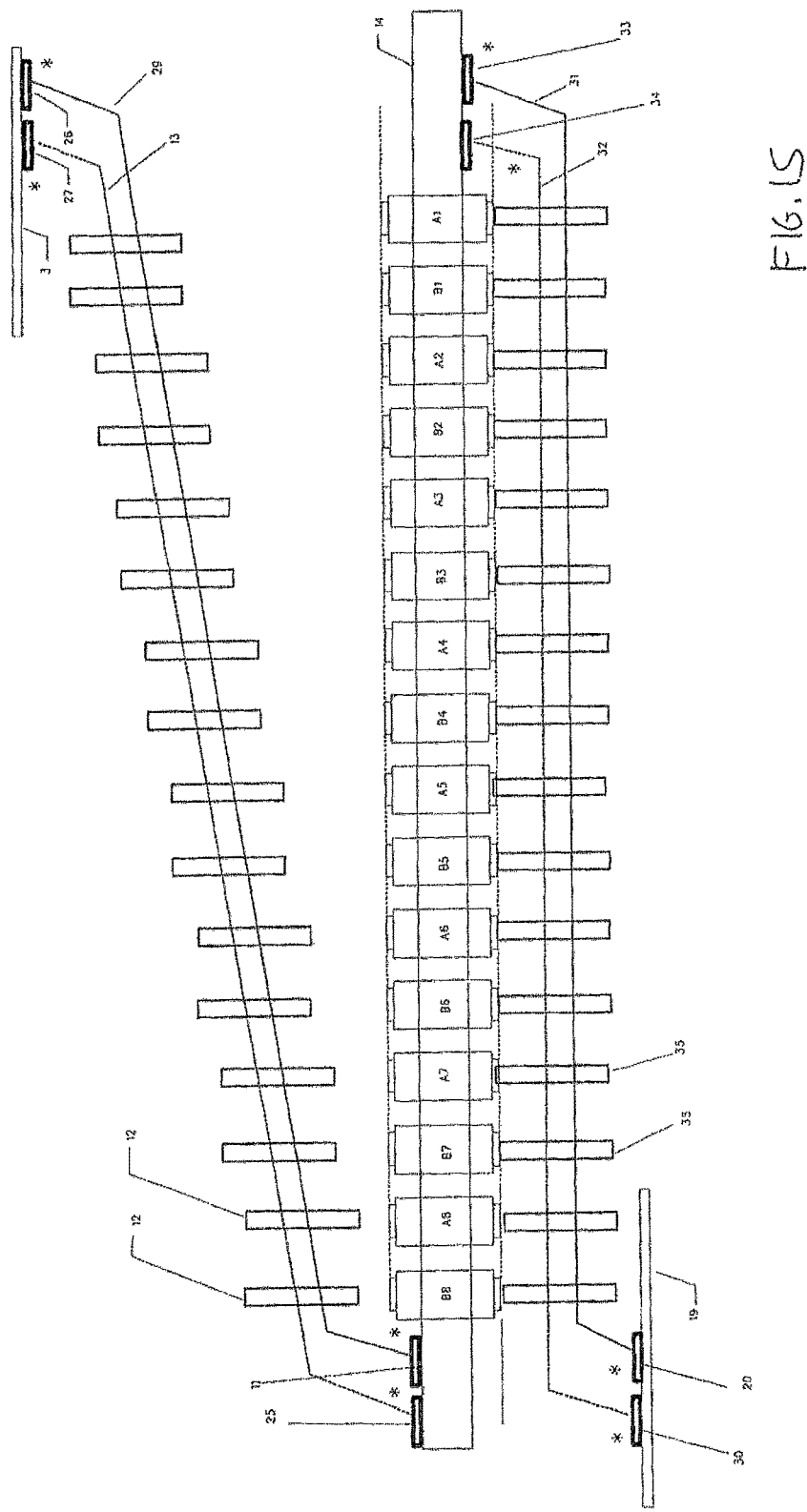

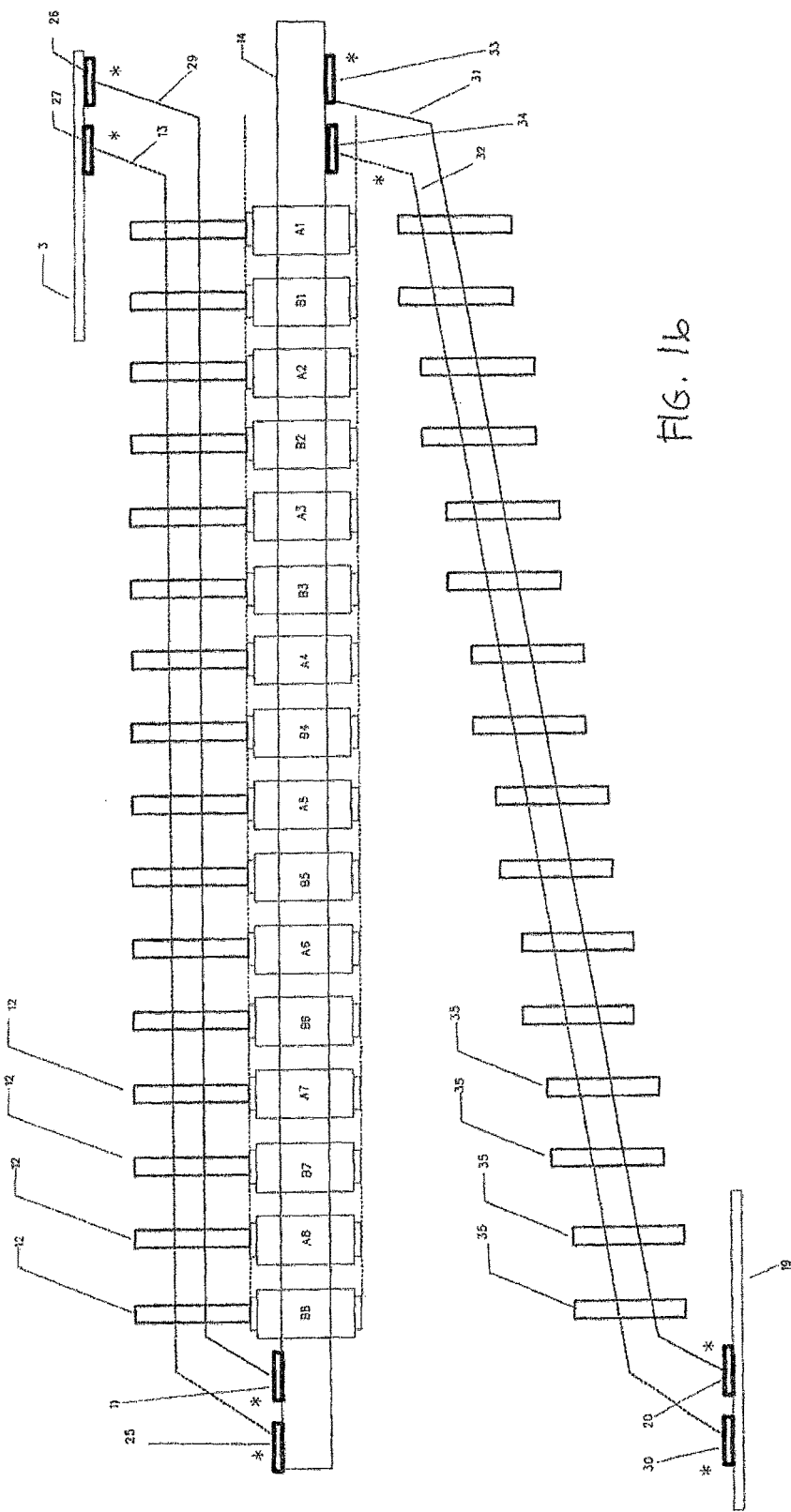

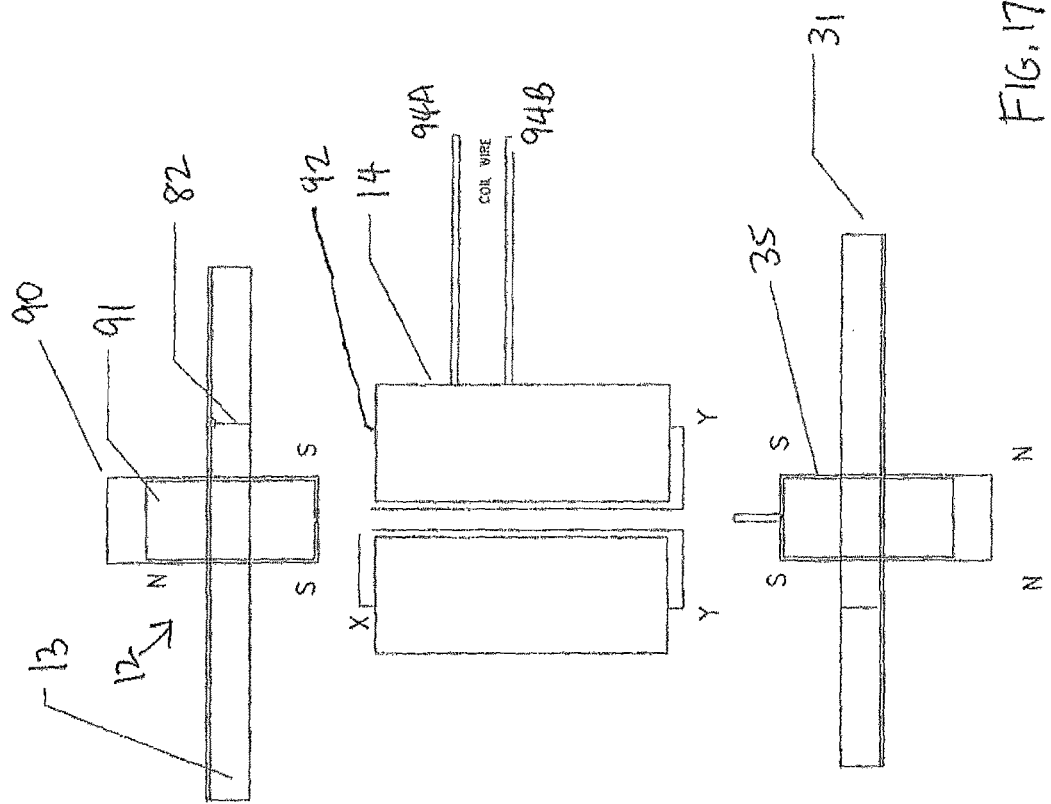

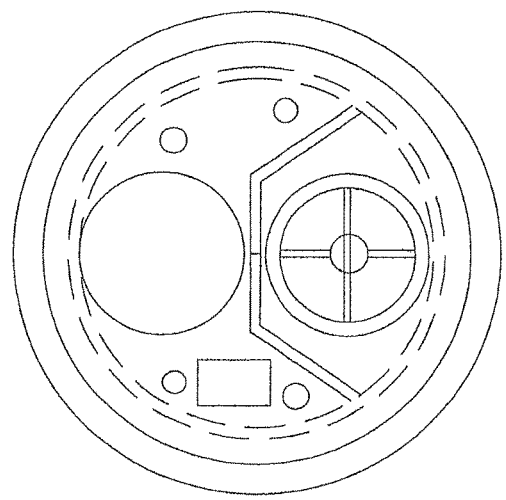
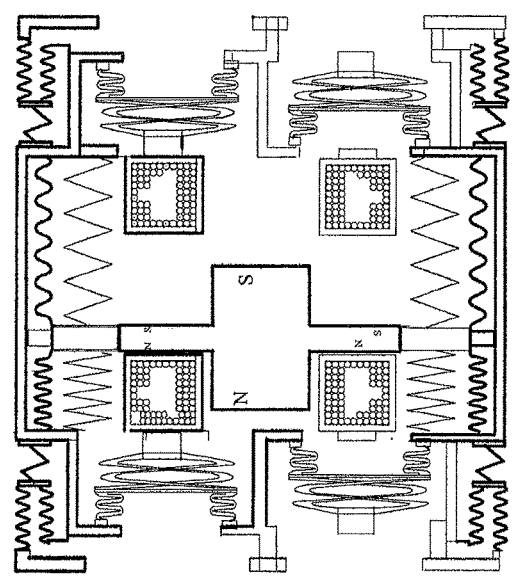
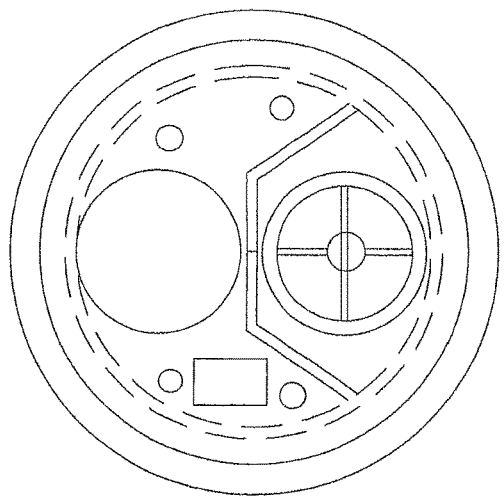
FIG. 19A

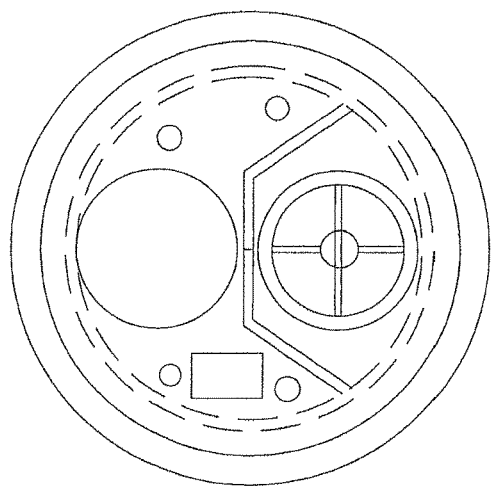
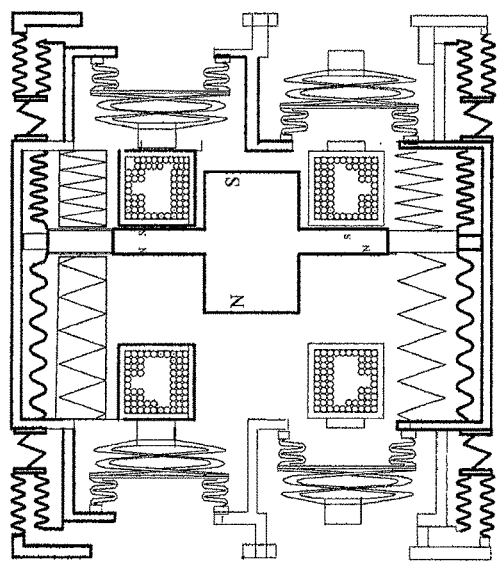
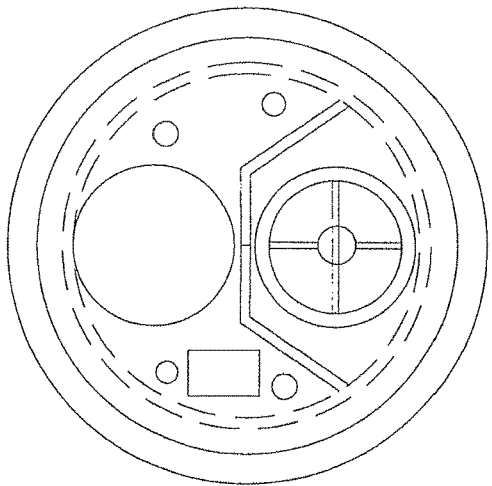
FIG. 19C

ARTIFICIAL HEART

BACKGROUND

Field of the Invention

The invention generally relates in some aspects to an artificial heart, components of an artificial heart, and methods of using the same.

Description of the Related Art

The heart is the muscle that drives the cardiovascular system in living beings. Acting as a pump, the heart moves blood throughout the body to provide oxygen, nutrients, hormones, and to remove waste products. The blood follows two separate pathways in the human body, the so-called pulmonary and systemic circulatory circuits. In the pulmonary circuit, the heart pumps blood first to the lungs to release carbon dioxide and bind oxygen, and then back to the heart. Thus, oxygenated blood is constantly being supplied to the heart. In the systemic circuit, the longer of the two, the heart pumps oxygenated blood through the rest of the body to supply oxygen and remove carbon dioxide, the byproduct of metabolic functions carried out throughout the body. The heart supplies blood to the two circuits with pulses generated by the orderly muscular contraction of its walls.

In order to keep blood moving through these two separate circulatory circuits, the human heart has four distinct chambers that work in pairs. As illustrated in FIG. 1, the heart 100 includes a right atrium 120, a right ventricle 140, a left atrium 160, and a left ventricle 180. One pair of chambers, the right ventricle and left atrium, is connected directly to the pulmonary circuit. In it, de-oxygenated blood from the body is pumped from the right ventricle 140 to the lungs, where it is oxygenated, and then back to the left atrium 160.

In the systemic circuit, the other pair of chambers pumps the oxygenated blood through body organs, tissues and bones. The blood moves from the left atrium 160, where it flows from the lungs, to the left ventricle 180, which in turn pumps the blood throughout the body and all the way back to the right atrium 120. The blood then moves to the right ventricle 140 where the cycle is repeated. In each circuit, the blood enters the heart through an atrium and leaves the heart through a ventricle.

Thus, the ventricles 140, 180 are essentially two separate pumps that work together to move the blood through the two circulatory circuits. Four check valves control the flow of blood within the heart and prevent flow in the wrong direction. A tricuspid valve 200 controls the blood flowing from the right atrium 120 into the right ventricle 140. Similarly, a bicuspid valve 220 controls the blood flowing from the left atrium 160 into the left ventricle 180. Two semilunar valves (pulmonary 240 and aortic 260) control the blood flow leaving the heart toward the pulmonary and systemic circuits, respectively. Thus, in each complete cycle, the blood is pumped by the right ventricle 140 through the pulmonary semilunar valve 240 to the lungs and back to the left atrium 160. The blood then flows through the bicuspid valve 220 to the left ventricle 180, which in turn pumps it through the aortic semilunar valve 260 throughout the body and back to the right atrium 120. Finally, the blood flows back to the right ventricle 140 through the tricuspid valve 200 and the cycle is repeated.

When the heart muscle squeezes each ventricle, it acts as a pump that exerts pressure on the blood, thereby pushing it out of the heart and through the body. The blood pressure, an indicator of heart function, is measured when the heart muscle contracts as well as when it relaxes. The so-called systolic pressure is the maximum pressure exerted by the blood on the arterial walls when the left ventricle of the heart contracts forcing blood through the arteries in the systemic circulatory circuit. The so-called diastolic pressure is the lowest pressure on the blood vessel walls when the left ventricle relaxes and refills with blood. One example of healthy blood pressure is considered to be about 120 millimeters of mercury systolic and 80 millimeters of mercury diastolic (usually presented as 120/80).

Inasmuch as the function of the circulatory system is to service the biological needs of all body tissues (e.g., to transport nutrients to the tissues, transport waste products away, distribute hormones from one part of the body to another, and, in general, to maintain an appropriate environment for optimal function and survival of tissue cells), the rate at which blood is circulated by the heart is a critical aspect of its function. The heart has a built-in mechanism (the so-called Frank-Starling mechanism) that allows it to pump automatically whatever amount of blood flows into it. Such cardiac output in a healthy human body may vary from about 4 to about 15 liters per minute (LPM), according to the activity being undertaken by the person, at a heart rate that can vary from about 50 to about 180 beats per minute.

Several artificial devices have been developed over the years to supplement or replace the function of a failing heart in patients. These include devices developed by companies as well as research institutions such as the Berlin Heart Institute, the Pennsylvania State University, the University of Utah, the Cleveland Clinic Foundation, the University of Perkinje (in Bruno, Czechoslovakia), the University of Tokyo, the Thoratec Corporation, Abiomed Inc., Novacor, and Symbion Inc. Typically, these artificial devices consist of pumps that aim at duplicating the required pumping functions of the left and right human ventricles. One method of actuation for these pumps has been through the pneumatic action of an external mechanism. See, for example, U.S. Pat. Nos. 4,611,578 and 5,766,207, which are hereby incorporated by reference in their entireties. Periodic pulses of compressed air drive the pumps at the desired pressure and rate of cardiac output. A moderate vacuum may be applied between pulses to allow more rapid refilling of the ventricles with blood flowing from the respective atrium.

One notable artificial heart currently in use as an implant for patients waiting for a heart transplant is the Total Artificial Heart manufactured by SynCardia Systems, Inc., of Tucson, Ariz. Designed to operate much the same way as a human heart, this artificial heart replaces the two active chambers (i.e., the ventricles) of the human heart with corresponding artificial components. As illustrated in FIG. 2, such artificial heart 300 includes two separate chambers or ventricles 320 and 340 that replace the right and left ventricles of the human heart, respectively. Each chamber is equipped with a respective diaphragm (360 and 380 in the right and left chamber, respectively) that has an air contact side and a blood contact side. Each diaphragm is designed as a spherical hemisphere. As shown in FIG. 3, the artificial heart 300 is implanted by connecting the top of the right chamber 320 to the right atrium 120 and the top of the left chamber 340 to the left atrium 160. The bottom of each chamber is provided with an air line (400 and 420 in the right and left chamber, respectively) that is embedded in the patient's body but extends outside for connection to a pneumatic driver.

When driven by a supply of pressurized air from the pneumatic driver, each diaphragm 360, 380 discharges blood from the respective chamber 320, 340 simulating the function of a ventricle. This phase is referred to in the art as systole or equivalently as the ejection phase. When the pressurized air is removed from the diaphragm, known as diastole or the filling phase, blood can enter the ventricle from the connected atrium. The rate at which blood enters the ventricle depends on the difference between the atrial pressure and the pressure on the air-side of the diaphragm. To increase this filling rate, a slight vacuum of about 10 mmHg is normally applied to the air-side of the diaphragm during diastole. Artificial valves 144a (tricuspid), 146a (bicuspid) and 144b (pulmonary), 146b (aortic) control the flow from the respective atrium into each artificial ventricle and out to the circulatory systems, respectively.

The pneumatic drivers used to date for driving all artificial hearts have been cumbersome and inadequate for affording patients any degree of independent mobility. They employ compressors, vacuum pumps, and air tanks coupled to electrically actuated valves, all of which amounts to a large and heavy apparatus that can only be transported on wheels and with considerable effort. Therefore, many attempts have been made during the last two decades to produce a portable driver for these devices. However, because of the complexity of the required functionality and the hardware necessary to produce it, pneumatic heart drivers continue to be bulky, require frequent maintenance, and often provide air pulses that do not match the performance of the larger drivers they are meant to replace. Even at the approximate weight of 20 pounds and size of about 0.7 cubic feet achieved so far, pneumatic drivers remain unwieldy and substantially not portable for a patient who is kept alive by an artificial heart.

In essence, a portable driver needs to be reliable, durable, easy to use, and sufficiently simple in design to be affordable. Unfortunately, each of these requirements contributes to the complexity of the design, which in turn has produced devices that are not sufficiently small and light-weight to be manageable in the hands of a patient. Furthermore, it is essential that the pneumatic driver be able to provide the correct pressure balance between the left and right ventricles of the artificial heart to ensure the proper operating pressure to the pulmonary and systemic circuits regardless of the speed of operation. Typically, this requires that the driver be able to operate so as maintain, on average, a right atrial pressure of about 9 mmHg, a mean pulmonary artery pressure of about 35 mmHg, a left atrial pressure of about 10 mmHg, and a mean aortic pressure of about 95 mmHg.

This need to provide different operating pressures to the right and left chambers (ventricles) of the artificial-heart device has not been met heretofore with a simple design suitable for a portable driver. For example, the blood pump described in U.S. Pat. No. 4,611,578 includes a configuration wherein two reciprocating pistons in a common cylinder may be operated alternatively to provide redundancy or independently to actuate two separate pneumatically driven blood pumps. This issue is not addressed in the patent, but it describes a sophisticated control system that arguably could be used to provide the correct operating pressure to each chamber of the artificial heart. However, the complex and multi-component structure of the device necessarily requires a relatively heavy and large apparatus, though described as portable. The commercially available module weighs about 25 pounds and is approximately 0.6 cubic feet in volume.

U.S. Pat. No. 5,766,207 describes another portable pneumatic driver for ventricular assist devices that could also be adapted for an artificial heart. The single pump of the invention could be used to drive both ventricles of an artificial heart, but only at the same pressure and volume rate. Thus, this device, even if modified to meet the other requirements of a portable artificial-heart driver, would not be suitable as an alternative to the stationary modules currently in use.

Therefore, there remains a strong need for an improved artificial heart that could serve as a permanent cardiac replacement. Preferably, the artificial heart and all of its associated components are completely implantable.

SUMMARY

Embodiments of artificial hearts as disclosed herein can have several potential advantages. The use of flat helical springs to align a bellows structure allows the structure to flex its size to pump blood, the multiple solenoids with floating magnetized rods and permanent magnet assemblies held by the flat helical springs provide the power; the artificial heart pumps blood with virtually no friction and no parts to wear out. The use of solenoids advantageously move blood in a gentle manner. The solenoids are controlled by the digital circuitry. The contraction force, release force, duration between forces, the rate of change of forces are all controlled by a microprocessor for optimum operation. This microprocessor program also minimizes energy consumption. By use of the multi-turn flat helical springs, the movement of each solenoid step is small and preset; this optimizes the force and efficiency of solenoid operation. The size and shape of the solenoid rod attached to the permanent magnet can be used to control and balance the solenoid power requirements between attracting and repelling the permanent magnet. The initial solenoid motion (e.g., linear distance moved between the solenoid and the spring magnet) and the ending solenoid motion are twice or at least twice the motion of the intervening solenoids; this is to ensure there is no accidental lock up of the solenoids. Use of a floating solenoid rod allows in some embodiments more contracting distance than would a solid rod. Solenoid drives can use regulated current pulsed operation in a low duty cycle. This drive system can provide extensive power if needed, up to 3 or 4 times or more the minimum drive power. Space is shared between atria and ventricles allowing for maximum flexibility and cardiac output; while the total atrioventricular volume is fixed, the range of ratios of atrial volume capacity to ventricular volume capacity can vary widely. Movement of the bicuspid valve and the mitral valve with designs as disclosed herein minimize blood movement (nearly all blood movement is axial), and provides little chance for damage to the blood cells. Motion of the blood within the artificial heart includes squeezing out or pulling in just like the biological heart, with normal space between the cells. There is no pinching of the blood cells which might cause damage. The arrangement of the flat helical springs, solenoid rod and solenoid is unique, and described in detail herein.

Further advantages of certain embodiments of artificial hearts as disclosed herein include incremental power operation. The arrangement of the permanent magnet locks can save energy. Also, the spring force constant of the flat helical springs enables the even distribution of force for every solenoid operation in the pump. Linear springs are preferred in some embodiments, but non-linear springs (e.g., a pair of non-linear springs) can also be utilized. Furthermore, the use of bellows between the atrial and ventricles, atria, ventricles, and as radial outer walls for the blood flow chamber, as well as solenoids to control the flow of blood by a programmed processor in digital increments offers virtually no friction, gentle operation and long operating life. Moreover, the use of bellows removes any sharp changes in pressure, and provides a good buffer for blood pressure transients minimizing their magnitude and duration. Also, large atriums allow constant inflow of blood. The use of cylindrical ventricles allows smooth, steady programmed pressure controlled output. The use of worked metal allows long life by minimizing fatigue stress effects. The use of incremental control and incremental feedback allows precision operation. The use of multiple turn flat helical springs permits the bending action to be small thus minimizing stresses while providing adequate incremental stroke length to contribute to the total volume of blood being pumped in each heart beat cycle. This artificial heart system has many back-up features so that any failure modes can be repaired and/or compensated for by the digital control circuitry.

In some embodiments, solenoids can be operated in push-pull mode, one at a time, independently or as a group or at the same time, depending on the program. These features speed up solenoid operation and allow very flexible programming.

In some embodiments, disclosed is an artificial heart that includes an outer housing defining a first chamber having a fixed volume. The chamber can include a right ventricle and a left ventricle separated by a single movable plate structure within the fixed volume. The movable plate structure can be coupled to the center of a magnet and configured to vary a right ventricular volume and a left ventricular volume inversely proportionally to each other upon movement of the movable plate structure. The artificial heart can also include a first spring assembly, and a second spring assembly operably connected to the magnet and the movable plate structure. The artificial heart can also include a first drive coil operably connected to a first end of the chamber and a second drive coil operably connected to a second end of the chamber. The first drive coil and the second drive coil can be configured to attract or repel the magnet, thereby moving the movable plate structure. In some embodiments, the first spring assembly and the second spring assembly can include a bellows spring operably connected to a helical spring. The first spring assembly and the second spring assembly can be configured to store energy and actuate the movable plate structure. The relative contribution to movement of the movable plate structure by the first spring assembly and the second spring assembly can increase when the relative contribution of the first drive coil and the second drive coil to the movable plate structure decreases. The movable plate structure can be configured to have a frictionless, noncontact predetermined first stop location when a magnetic contraction force from the magnet is in equilibrium with the force from the first spring assembly and the first drive coil. The movable plate structure can be configured to have a frictionless, noncontact predetermined second stop location when a force from the second spring assembly is in equilibrium with the force from the magnetic contraction force in the opposite of the first stop position. The first drive coil can drive a control. The artificial heart can also include a second chamber that includes a left atrium and a third chamber that includes a right atrium. The left atrium and the right atrium can be fluidly connectable to the first chamber, the second chamber and the third chamber and configured to receive continuous blood flow, as well as have a preset pressure controlled profile. The left atrium and the right atrium can be configured such that blood flow through the left atrium and the right atrium can flow into the left ventricle and right ventricle respectively allowing mechanical actuation of the magnet by the blood flow.

In some embodiments, there are no wires within the fixed volume, preventing loose connections or cables within the fixed volume. In some embodiments, the artificial heart can further include an aortic valve configured to be connected to a patient's aorta, and a pulmonic valve configured to be connected to a patient's pulmonary artery. In some embodiments, the aortic valve cross-sectional area is large and about or at least about 5%, 10%, 15%, 20%, or more of the cross-sectional area of the first chamber. In some embodiments, the magnet is a high coercivity, high flux density magnet, such as, for example, a neodymium iron boron magnet.

Also disclosed herein is an artificial heart that can include an outer housing. The outer housing can include a right heart valve plate and a left heart valve plate spaced axially apart by a first bellows spring and a second bellows spring. The artificial heart can also include a solenoid connected to a first drive coil and a second drive coil. The first drive coil can be operably connected to the right heart valve plate and the second drive coil operably connected to the left heart valve plate. The artificial heart can also include a magnet operably connected to a plate structure spaced axially between the first drive coil and the second drive coil. The magnet can be operably connected to a first end of the first bellows spring and a first end of the second bellows spring. The magnet can be configured to move axially upon activation of the first drive coil and the second drive coil resulting in conversion of electrical energy to mechanical energy, thereby axially elongating one of the first bellows spring and the second bellows spring and simultaneously contracting the other of the first bellows spring and the second bellows spring resulting in the release of energy, moving blood in or out of the heart by movement of the plate structure. The artificial heart can also include at least one sensor configured to determine at least one of the position, velocity, and direction of travel of the magnet. The artificial heart can also include a servomechanism controller configured to receive data from the sensor and control power to the first drive coil and the second drive coil, thereby actuating the magnet and the plate structure. The servomechanism controller can be configured to provide precise control of the position and speed of the magnet, such as at all times. The solenoid can be configured to actuate the magnet during periods of relative efficiency. The artificial heart can be made of an appropriate material, such as biocompatible titanium for example. Axial movement of the magnet in a cranial direction can increase a volume capacity of ventricles of the heart by a first amount while decreasing a volume capacity of the atria by the same first amount. The outer housing can be rigid. The controller can include a high gain, phase lock digital servomechanism feedback system. The controller can also be configured such that the plate structure is in very close proximity to, but never physically touches the left heart valve plate or the right heart valve plate during normal operation, thus acting as a virtually frictionless pump and increasing operating life. The controller can also be configured such that plate structure is separated by a minimum of about 0.1 mm with respect to the left heart valve plate or the right heart valve plate during normal operation. The artificial heart can also include discrete left and right atrial chambers with controlled pressure and range of operation, which can be axially movable plates. Any or all of the chambers can be relatively large, and be configured to reduce restrictions on blood flow, as well as configured to control pressure and range of operation. The artificial heart can also be configured such that blood flow through the artificial heart directly cools the first solenoid and the second solenoid. The artificial heart can also include one, two, or more sensors, configured to determine at least one of blood pressure, blood oxygen level, and blood temperature. The controller can be configured to receive data regarding at least one of blood pressure, blood oxygen level, and blood temperature, analyze the data, and adjust power to the first drive coil and the second drive coil accordingly. The artificial heart can include, or have an outer housing that is a rigid structure. Each of the drive coils, heart valve plates, sensors, and sensor wires can be mounted to the artificial heart. The artificial heart may not include any loose wires or sensors. The artificial heart can be configured to minimize force on the parts when the artificial heart is beating.

BRIEF DESCRIPTION OF THE DRAWINGS

FIG. 3A is a schematic view of the fully implantable heart of the present invention.

FIG. 4A illustrates a schematic side view of one embodiment of an artificial heart having a single spring.

FIG. 4B is a cross-sectional view through line B-B of FIG. 4A looking from a generally cranial to a generally caudal direction.

FIGS. 4C-4E illustrate views of another embodiment of an artificial heart with large discrete atria.

FIG. 5 is a two-dimensional schematic incline plane representation of the actual three-dimensional helical spring and solenoid ring.

FIG. 6A is a schematic side view of the helical spring as previously described in a fully uncompressed configuration.

FIG. 6B illustrates the spring of FIG. 6A in a fully compressed configuration.

FIG. 6C is a top view illustrating a plurality of solenoids 1A-16A within solenoid ring.

FIGS. 7A-7B illustrate another embodiment of an artificial heart having a plurality of springs.

FIG. 9A is a schematic side view of the helical springs forming a double helix.

FIG. 9B illustrates the springs of FIG. 9A in a fully compressed configuration.

FIG. 9C is a top plan view of the helical spring of FIG. 9A.

FIG. 10A-10B schematically illustrate a close-up detail view of a helical spring according to some embodiments of the invention.

FIG. 11 illustrates several consecutive segments of the non-linear spring illustrated in FIGS. 10A-10B.

FIGS. 12A and 12B illustrate a top view and side view, respectively of a non-linear helical spring 13 as previously described, with coupled magnetic rods.

FIGS. 14A-14D illustrate another embodiment of an artificial heart, with spring assemblies positioned near both the cranial and caudal ends of the artificial heart, and the solenoid assembly is positioned longitudinally therebetween.

FIGS. 15-16 is a two-dimensional schematic incline plane representation of the actual three-dimensional atrial helical springs and ventricular helical springs and solenoid ring.

FIG. 17 illustrates more details of a "push-pull" solenoid assembly similar to that of FIG. 13, with features as described in connection with FIGS. 14A-16 above.

DETAILED DESCRIPTION

Disclosed herein is an artificial heart designed to be implanted in the human or other animal body and offers long operating life. The heart requires only occasional external electromagnetic connection exterior to the body to recharge an internal battery also implanted in the body. The use of flat helical linear or non-linear springs in some embodiments provides lateral stability, providing a type of alignment spine to the moving parts of the heart, primarily the heart chambers' inner and outer bellows which are held in place, top and bottom, by the flat circular plates at top and bottom of the artificial heart. These top and bottom plates are also secured to a solid housing, e.g., a cylinder, made of metal in some embodiments, completing the enclosure of the heart. The lateral stability of the moving springs assures freedom from sliding friction between the springs and both sets of bellows. Solenoids with permanent magnetic rod assemblies held by the flat helical springs provide the power for the artificial heart to pump blood with no sliding friction and no parts to wear out. Implantable units can be enclosed in one, two, or more biocompatible materials, such as a metal well known to be tolerated by the human body. Types of metals contemplated for use in certain embodiments as disclosed herein include but are not limited to steel (e.g., stainless steel), tungsten, titanium, and platinum. Other possible metals could include, for example, tantalum, gold, palladium, silver, nickel, cobalt, copper, or chromium. The metals can be alloys, such as Nitinol or Elgiloy, and can be combinations of metals. Other type of materials include a biocompatible polymer such as ePTFE or PTFE for example.

The heart is designed for long life and low energy consumption. Operation of the artificial heart operation is similar to that of the native heart. It has four chambers, and four valves that may be, for example, a ball-type, tilting-disc, bileaflet, trileaflet, or biological valve. The valves could be mechanically activated, electronically activated, or a combination of the above. The artificial heart pulls in blood and ejects blood, and can be programmed by bio-feedback signals which direct digital circuitry to provide precise control of each solenoid as the blood moves into the atria, then the ventricles and finally exits to the body's arteries. In this process blood flow is gentle and virtually completely axially flowing, minimizing any radial and turbulent motion and pinching of the blood cells, that could cause undesired hemolysis or clotting. The biofeedback control system can be set up immediately after implantation. After implantation, modifications to the control system parameters can be made externally to adapt the system to changing needs of individual patients. Such external changes augment the constant internal biofeedback system used to control individual current pulses applied to each solenoid.

Figure 1:
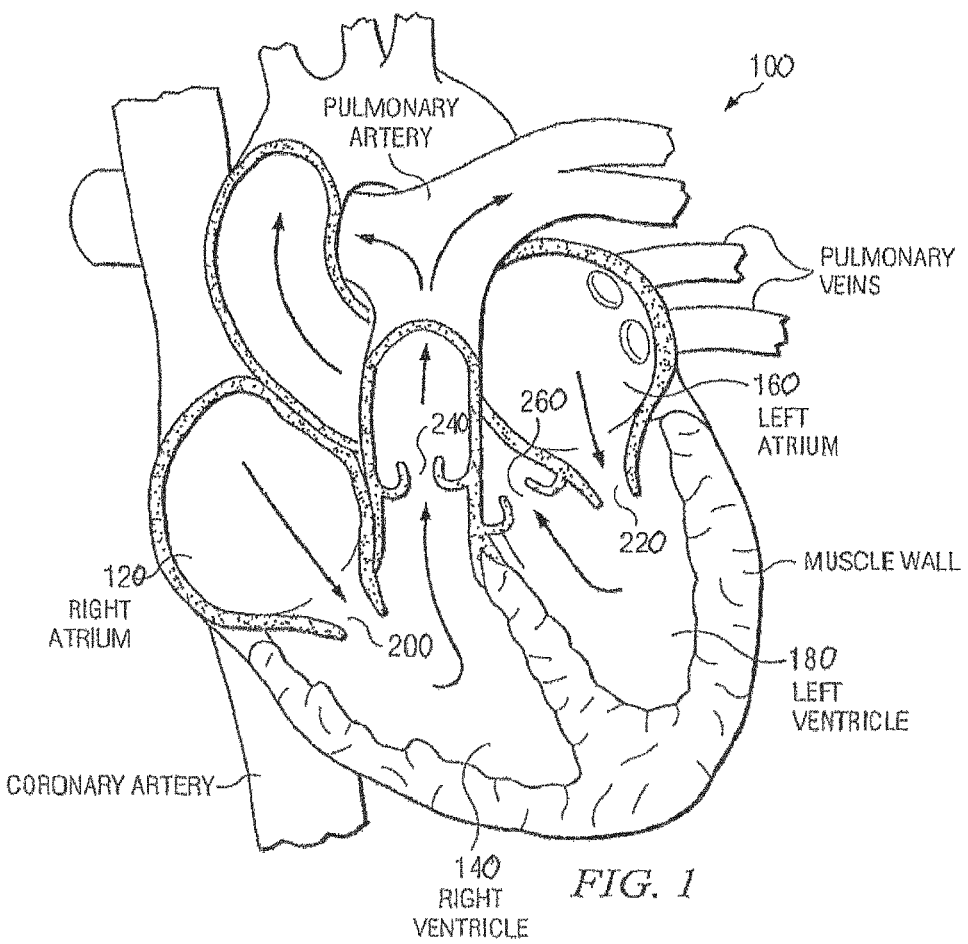
FIG. 1 is a representation of the human heart.
Figure 2:
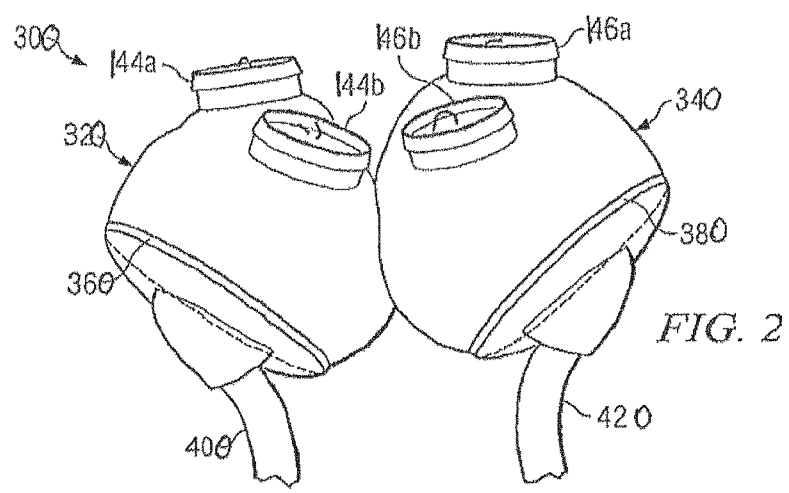
FIG. 2 is a schematic view of a prior art artificial heart.
Figure 3:
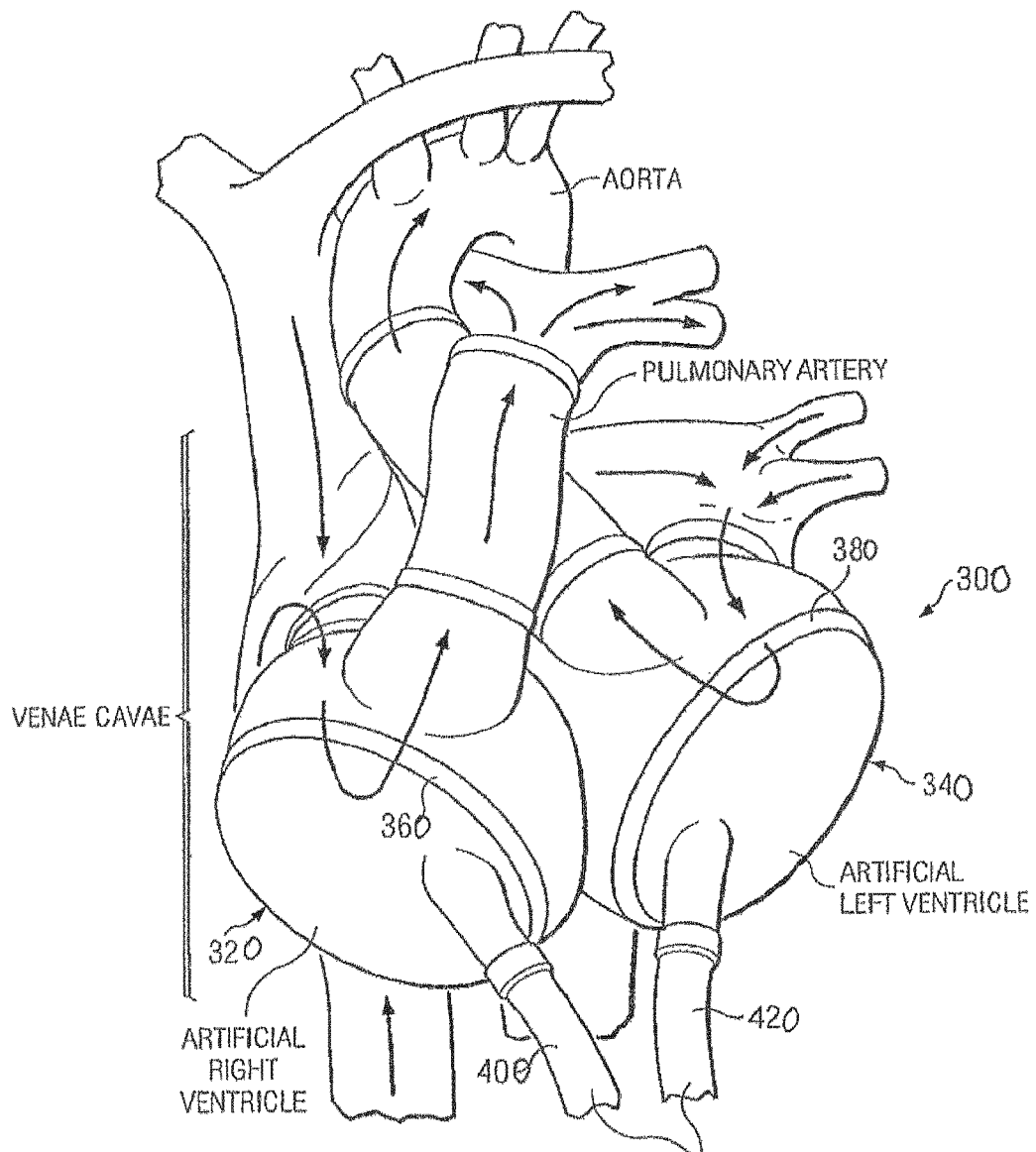
FIG. 3 is a representation of the artificial heart of FIG. 2 connected to the cardiac atria of a human body.

FIG. 3A illustrates schematically certain components of an artificial heart system 50 with respect to a patient 1000, according to some embodiments of the invention. While shown as discrete modules, it will be appreciated that various modules can be integrated together or separated according to the desired clinical result. In some embodiments, an artificial heart system 50 includes an external power supply 99. This can be in some cases a relatively large power supply which patients can use at home or at work while resting and sleeping. It can also be built more compactly as, for example, a belt with 8 hours or more of battery energy. The artificial heart system can also include a wireless energy (e.g., induction) transfer system 98. In some embodiments, this system includes a plurality of coils (e.g., 2 coils), one internal and one external which transfer energy via magnetic field through the skin without physically piercing it. The internal coil receives the energy sending it to the rectifier and regulator in the internal battery enclosure. Fairly high frequency can be used to minimize size, such as, for example, between about 300 kHz to 3000 kHz, between about 500 kHz to about 2000 kHz, or at least about 1000 kHz, 2000 kHz, 3000 kHz, 4000 kHz, 5000 kHz or more, however, any suitable frequency can be utilized depending on the desired result.

The system can include an internal power source 97, such as a rechargeable battery and a regulator. In some embodiments, the system provides over about or at least about one, two, three, four, or more hours of battery life in normal use, although other battery capacities are also possible. The regulator can provides fast battery charging, such as about three hours or less in certain cases. An internal control unit 96 contains a microprocessor programmed to control the heart motion control electronics. This hardware and/or software controller includes a transceiver used to control externally heart operations as well as to transmit heart status signals including, for example, diastolic and systolic pressure waveforms, oxygen content of the blood waveform, heart rate waveform and battery condition.

Complete heart condition is available at a glance when interrogated, such as via an external device 1002 which may be a computer, tablet, mobile phone, PDA, database, electronic health records system, or the like that are configured to receive such data from the internal control unit 96. In various embodiments, the internal control unit 96 may communicate wirelessly with an external device 1002 via a protocol such as 802.11x, WiFi, Bluetooth, Zigbee, and/or via cellular networks.

In some embodiments, the internal control unit 96 is in operative communication with various biosensors or probes, for example, sensors that can detect pH, $pCO_2$, $pO_2$, pressure, and temperature. Cardiac output (CO) can be calculated by combining two $pO_2$ measurements obtained from a pair of probes, one disposed in an artery and the other in a vein. Alternatively, or in addition to the aforementioned sensors, sensors for other blood parameters such as potassium, sodium, calcium, bicarbonate, urea nitrogen, creatinine, bilirubin, hemoglobin, glucose, and lactate can also be in operative communication with the internal control unit 96. Some biosensors or probes that can be used in connection with embodiments herein are described, for example, in U.S. Pat. Pub. No. 2010/0057046 to Stevens et al. which is hereby incorporated by reference in its entirety.

The sensors placed in the heart in continuous high-speed high-resolution digital form closely monitor the operation of the heart. The systolic pressure and diastolic pressure can be measured as each solenoid closes or opens. A small change in any solenoid operation could be detected. Thus, problems can be detected as they happen. The oxygen content of the blood can also be measured in every heartbeat. This can measure the effectiveness of the body to assimilate the oxygenated blood being pumped and control the heart rate. No power will be wasted by over or under driving the heart. The power drive to the solenoids has more than 3 to 4 times the force required to drive the solenoids thus full control of the solenoids is achieved. The solenoids in the helical spring(s) can be operated independently to correct problems. Power can be increased or decreased accordingly for the needs of each solenoid. The control program can be instantaneously changed with remote sensors to vary the oxygen level or blood pressure level as needed. In some embodiments, a system includes a biofeedback loop can also include interpreting the physiologic parameter feedback information; and adjusting a setting such as heart rate or contractility of the artificial heart 50 at least partially based on the physiologic parameter feedback information. In some embodiments, one, two, or more biosensors can detect sympathetic nervous system activity in the brain, spinal cord, or circulating levels of catecholamines such as epinephrine and norepinephrine; parasympathetic nervous system activity such as vagus nerve tone; carotid sinus, aortic arch, and other baroreceptor activity; kinetic activity such as increased extremity movement; ATP production; mitochondrial activity; or other cellular activity sensors; and send signals to the internal control unit 96 which could be configured to increase or decrease heart rate and/or contractility of the artificial heart 50, for example, accordingly. In one embodiment, a sensor measuring a drop in blood pressure or peripheral vascular resistance would send signals to the internal control unit 96, which could send signals to the artificial heart to increase heart rate and/or contractility.

The internal battery is also closely monitored. The charge rate and discharge rate and voltage variation between them allows prediction of the battery life, and energy remaining in the battery. The battery can be recharged or replaced before complete discharge or failure.

The artificial heart mechanism contains the solenoids, spring and permanent magnet pumping mechanism, as discussed further herein. The artificial heart, as disclosed herein can be a permanent replacement for a failing heart, such as congestive heart failure due to ischemic, dilated, restrictive, or other cardiomyopathies. It operates quite similarly to a biological human heart. An artificial heart can have four chambers and four valves, and lack any pistons in some embodiments. The artificial heart contracts and ejects the blood for distribution to the rest of the body just like the human heart, causing minimal to no damage to circulating blood cells, and may or may not require the use of anticoagulant therapy. The artificial heart is designed to operate for years, and up or exceeding the natural life of a patient, unlike conventional artificial hearts which are generally intended to be temporarily placed as a bridge to a heart transplant. It can be programmed for changing needs as the patient's requirements change. It has low power consumption allowing the patient long operating periods without an external battery, using only the internal battery, offering operating intervals measured in hours rather than minutes.

Several modes of operation are possible, depending on the desired clinical result. FIG. 4A illustrates a schematic side view of one embodiment of an artificial heart 50. The artificial heart includes an outer housing 5 that may take the form of a cylinder, although other ellipsoid, spherical, cubical, or other geometric configurations are also possible. Outer housing 5 includes one or more sidewalls 51, as well as top plate 3 and bottom plate 19. Top plate 3 can include apertures to allow for blood flow into the artificial heart 50 via the superior vena cava 1, inferior vena cava, and pulmonary vein 2. Bottom plate 19 can include apertures for blood flow out of the artificial heart 50 via the aorta 60 and the pulmonary artery 61. In some embodiments, the sidewall 51, top plate 3, and bottom plate 19 are rigid or relatively rigid structures.

In some embodiments, the outer housing 5 of the artificial heart has a maximal longitudinal dimension of between about 3" and about 7" in longitudinal dimension, or no more than about 6", 5.5", 5", 4.5", 4", 3.5", 3" or less inches in longitudinal dimension; a maximal transverse dimension of between about 2" and about 5", or no more than about 6", 5.5", 5", 4.5", 4", 3.5", 3" or less in transverse dimension; and between about 1.5" and about 3.5" in thickness, or no more than about 5", 4.5", 4", 3.5", 3", 2.5", 2", or less in thickness.

With respect to the right-sided circulation of the patient, deoxygenated blood from the body including the legs, arms, head, and torso enters the artificial right atrium 6 of the artificial heart 50 via either the superior vena cava 1 or the inferior vena cava (not shown). The deoxygenated blood then travels through the tricuspid valve 8 into the right ventricle 15, through the pulmonic valve 17 and out into the pulmonary artery 61, where the blood can then be reoxygenated in the lungs. With respect to the left-sided circulation of the patient, reoxygenated blood from the lungs enters the left atrium 7 via the pulmonary vein 2. The reoxygenated blood then travels through the mitral valve 9 into the left ventricle 16, through the aortic valve 18, and out the aorta 60, to perfuse the rest of the body. Blood inflows into the atria 6, 7 are facilitated by a pressure gradient caused by movement of the axially movable plate 10 in a generally caudal direction.

Axially movable plate 10 houses the mitral valve 9 and the tricuspid valve 8 therethrough. Axially movable plate 10 is operably attached, such as on its caudal surface at attachment point 11, to a first end of a helical spring 13. While the embodiment illustrated shows only a single helical spring 13, other embodiments described elsewhere herein describe a plurality of springs, such as 2, 3, 4, or more springs. Spring 13 is operably attached to a plurality of magnets 12 at various regularly or irregularly spaced apart locations along the length of the spring 13.

Within the artificial heart 50, an atrial septal wall 21 separates the left atrium 7 from the right atrium 6, while a ventricular septal wall 24 separates the left ventricle 16 from the right ventricle 15. Outer atrial wall 21 separates the atria 6, 7 from an outer chamber 4 between the atria 6, 7 and the outer sidewall 51 of the artificial heart 50. Outer ventricular wall 23 separates the ventricles 15, 16 from a working space 4 between the ventricles 15, 16 and the outer sidewall 51 of the artificial heart 50. Walls 21, 22, 23, and 24 in some embodiments are made of a flexible biocompatible material to form bellows structures. The bellows structure may be made, for example, of a polymer such as PTFE or ePTFE, or a metallic material such as titanium or Nitinol. Housed within the outer chamber 4 is a solenoid ring 14, which is operably attached at attachment point 20 to a second end of the helical spring 13. Solenoid ring 14 could be circular or ovoid in shape in some embodiments, although non-arcuate shapes such as a square, rectangle, and the like could also be utilized.

FIG. 4B is a cross-sectional view through line B-B of FIG. 4A looking from a first, e.g. generally cranial to a second, e.g. generally caudal direction. The solenoid ring 14 (housed radially in between sidewall 51 of outer housing 50 and outer ventricular wall 23) contains a plurality of solenoids, such as 16 solenoids as shown. However, other embodiments could include, for example, between about 2-64 solenoids, 4-32 solenoids, or 8-24 solenoids for example. These solenoids are marked 1A through 16A as illustrated, and the consecutively numbered solenoids, e.g., 1A and 2A, are spaced about 67.5 degrees apart, with adjacent solenoids spaced about 22.5 degrees apart along the circumference of the solenoid ring 14, although a number of other regular and irregular spacings are also envisioned. As noted previously, the helical spring 13 is connected to the moveable plate 10 at position 11 and to the solenoid ring assembly 14 at position 20.

FIG. 4C illustrates a portion of an artificial heart 700 similar to the artificial heart described and illustrated in connected with FIGS. 4A-4B, but also including two discrete, relatively large atria: right atrium 719 and left atrium 720, of which blood can enter via respective right atrial entry portal 701 and left atrial entry portal 702. The atria 719, 720 can be configured to be independently controlled. The right atrial pressure can be controlled by the action of opposing helical springs 713, 717. The left atrial pressure can be preset controlled by the action of opposing helical springs 723, 725. The size of the atria can vary and be defined by right atrial moving plate 715 and left atrial moving plate 722, which serve to move blood into respective right ventricle 705 and left ventricle 714. The right atrium can also include bellows 712, 718; the left atrium similarly includes bellows 721, 726. Also illustrated (and described in connection with other embodiments herein) are pulmonary valve 704, right ventricle 705, solenoids 706 (any number, such as 16 solenoids as described elsewhere herein), tricuspid valve 707, left ventricular bellows 708, aortic valve 709, left ventricle moving plate 710, mitral valve 724, and right ventricular bellows 727. Also shown is solenoid ring assembly 710, which along with the bellows and helical springs can be configured for purely axial movements, to hold the system together, and prevent parts from sliding against each other, resulting in a long operating life for the artificial heart 700.

FIG. 4D is a top view at the level of line A-A of FIG. 4C. Illustrated schematically are right atrial entry portal 701 and left atrial entry portal 702, and artificial heart housing 703. FIG. 4E is a cross-sectional view through line B-B of FIG. 4C. Illustrated schematically are right ventricular bellow 727, right ventricle 705, left ventricular bellow 708, left ventricle 714, pulmonary valve 704, aortic valve 709, solenoid ring assembly 710, and solenoids 706.

FIG. 5 is a two-dimensional schematic incline plane representation of the actual three-dimensional helical spring 13 and solenoid ring 14 as previously illustrated and described. As noted previously, cranial end of the spring is attached to axially movable plate 10 at attachment point 11, while the caudal end of the spring 13 is attached to the solenoid ring plate 14 at attachment point 20. The spring 13 is operably connected to a plurality of magnets (e.g., magnet rods 12) spaced apart along the length of the spring, each magnet 12 corresponding to a particular solenoid 1A-16A, such as in a 1:1 ratio of magnets 12 to solenoids 1A-16A. As the solenoids 1A-16A are energized one by one in a predetermined series, each solenoid will magnetically attract a corresponding magnet rod 12, and as such the spring 13 is forced progressively in a caudal direction along with the axially movable plate 10, causing blood to flow out of the ventricles 15, 16 during systole. For example, when solenoid 1A is energized, the solenoid 1A will pull a corresponding magnet rod 12 in a second, e.g. caudal direction such that the magnet rod 12 locks on the solenoid 1A. This incremental motion moves the entire spring structure 13 stepwise in a caudal direction. The power is then removed from solenoid 1A while, at the same time, solenoid 1A comprises a complementary permanent magnet that has an attractive force on the magnet rod 12 that is sufficiently strong to hold the rod 12 in place in the solenoid 1A after power is removed from the solenoid. Power is next applied to solenoid 2A, the time interval (either regular or irregular) between the applied power pulses and the amount of power applied is set by the digital control program to minimize power consumption and to provide the required blood pressure. In some embodiments, the total time to activate all solenoids such that the spring 13 moves from a fully expanded configuration to a fully compressed configuration is between about 50 msec to about 1,000 msec, such as between about 100 msec and about 800 msec. This sequence will continue until all solenoid rods and coils are locked together. The distance between the movable plate 10 and solenoid ring 14 closes step by step in a balanced fashion as each solenoid locks to its permanent magnet. Blood is ejected out of the right ventricle 15 and left ventricle 16 via pulmonic valve 17 and aortic valve 18 respectively. In some embodiments, the maximum axial distance that the movable plate 10 can travel is between about 2 inches and about 6 inches, or between about 3 inches and 5 inches. In some embodiments, the movable plate 10 can travel axially up to 50%, 60%, 70%, 80%, 85%, 90%, 95%, or more of the maximal longitudinal dimension of the artificial heart 50.

After a brief and predetermined interval, the blood from ventricles 15, 16 having been ejected into the pulmonary artery 61 or aorta 60 and retrograde flow being checked by the pulmonic 17 and aortic 18 valves respectively, the solenoids 1A-16A will begin to remove their magnetic hold on its corresponding rod 12. This is done by applying power to the solenoid 1A-16A in the reverse sequence and direction as when attracting the magnetic rod 12 to the respective solenoids 1A-16A. This is accomplished by applying a current pulse to solenoid e.g., 16A, of opposite polarity and to the remaining solenoids, stepwise and in reverse order. As each solenoid 1A-16A releases its lock on corresponding magnet 12 it pushes the plate 10 in a first, e.g., cranial direction step by step, in a balanced fashion. The spring force and systolic pressure force maintain the plate 10 in a cranial orientation during diastole. By balanced is meant to energize the solenoids not necessarily in numerical sequence (although numerical sequence energization is possible) but by energizing every fourth solenoid in an embodiment having 16 solenoids (although other predetermined sequences, such as adjacent solenoids, or every second, third, fifth, sixth, eighth, etc. solenoid could be energized depending on the desired clinical result) and then returning to advance one more and then energize succeeding fourth solenoids etc. until all 16 solenoids have been energized.

When the axially movable plate 10 moves in a cranial direction, the pressure in the ventricles 15, 16 is reduced, the tricuspid valve 8 and mitral valve 9 will open and allow in the blood flows from atria 6, 7 into ventricles 15 and 16 respectively. It should be noted that the blood is almost continuously flowing into the atria. The variable atrial volume capacity advantageously provided by axially movable plate 10 allows an extra buffer allowing for continuous blood flows into the atria 6, 7.

After the moveable plate 10 moves to its maximum extent in a cranial direction and spring 13 is in an unstressed, uncompressed configuration, the artificial heart 50 is ready to begin its next heart beat cycle. Use of the terms up and down, or superior and inferior herein refers to the normal position of the heart in an upright patient, while cranial (toward the patient's brain) and caudal (toward the patient's feet) account for orientation of the heart with the patient in other positions as well. However the heart 50 will generally operate properly in positions other than upright since gravitational forces are small compared to the solenoid initiated forces.

FIG. 6A is a schematic side view of the helical spring 13 as previously described in a fully uncompressed configuration, having longitudinal dimension X2. Not all magnetic rods 12 are illustrated for simplicity. FIG. 6B illustrates the spring 13 of FIG. 6A in a fully compressed configuration, with magnetic rods 12 locked down to their respective solenoids 14, and the spring 13 having longitudinal direction X1. In some embodiments, uncompressed dimension X2 is at least about 2×, 3×, 4×, 5×, 6×, 7×, 8×, 10×, or more with respect to the compressed dimension X1. FIG. 6C is a top view illustrating a plurality of solenoids 1A-16A within solenoid ring 14.

FIGS. 7A-7B illustrate another embodiment of an artificial heart 70. Artificial heart 70 is similar to artificial heart 50 having various components as illustrated in FIGS. 4A-4B, one difference being that instead of only having a single spring 13, a plurality of springs 13, 26 are utilized, which can be flat helical springs forming a double helix pattern, the first spring 13 and the second spring 26 in some embodiments sharing a common longitudinal axis, and differing by a translation along the axis. A first spring 13 is operably attached at its cranial end to axially movable plate 10 at attachment point 11, and operably attached at its caudal end to solenoid ring assembly 14 at attachment point 20. Similarly, a second spring 26 is operably attached at its cranial end to movable plate at attachment point 25, and operably attached at its caudal end to solenoid ring assembly 14 at attachment point 27.

FIG. 7B is a cross-sectional view through line B-B of FIG. 7A looking from a generally cranial to a generally caudal direction. The solenoid ring 14 contains a plurality of solenoids labeled 1A-8A and 1B-8B, such as 16 solenoids as shown or another desired number as previously disclosed.

Figure 8:
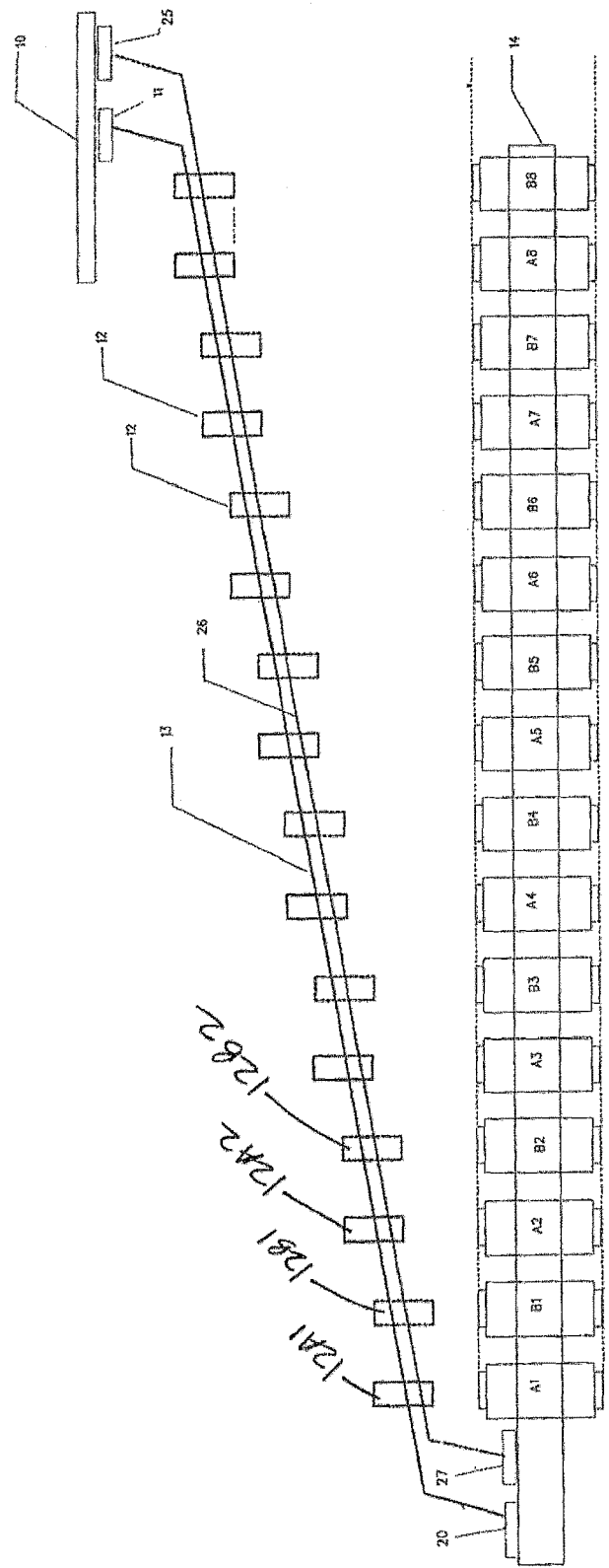
FIG. 8 is a two-dimensional schematic incline plane representation of the actual three-dimensional helical springs and solenoid ring.

FIG. 8 is a two-dimensional schematic incline plane representation of the actual three-dimensional helical springs 13, 26 and solenoid ring 14 as previously illustrated and described. As noted previously, cranial end of the first spring 13 is attached to axially movable plate 10 at attachment point 11, while the caudal end of the first spring 13 is attached to the solenoid ring plate 14 at attachment point 20. Cranial end of the second spring 26 is attached to axially movable plate 10 ant attachment point 25, while the caudal end of the second spring 26 is attached to the solenoid ring plate 14 at attachment point 27. Each spring 13, 26 is operably connected to a plurality of magnets (e.g., magnet rods 12 connected to first spring 13, and magnet rods 12' connected to second spring 26) spaced apart along the length of the springs 13, 26, each magnet 12, 12' corresponding to a particular solenoid 1A-8A or 1B-8B respectively, such as in a 1:1 ratio. In the aforementioned embodiment with 16 magnets and 16 solenoids, first spring 13 is connected to 8 magnets while second spring 26 is also connected to 8 magnets, although the first spring 13 could also have more or less magnets than the second spring 26 depending on the desired clinical result.

In some embodiments as illustrated, a plurality of solenoids can be energized simultaneously. When solenoids A1 and B1 are energized at the same time, the coil A1 will pull the permanent magnet rod 12A1 in a caudal direction locking on the solenoid A1 and solenoid B1 will pull the magnet rod 12B1 in a caudal direction to lock on the solenoid B1. This incremental movement moves the entire spring structure 13 and spring structure 26 at same time and same distance. The power is then removed from the solenoid coils A1 and B1. The permanent magnet's attractive force on the rod is sufficiently strong to hold the rods in place on the solenoid after power is removed from the solenoids. Power is next applied to solenoids A2 and B2 to attract magnets 12A2 and 12B2 respectively, the time interval between the applied power pulses and the amount of power applied is set by the digital control program to minimize power consumption and to provide the required blood pressure. This sequence will continue until all magnetic rods 12 and solenoid coils A1-A8 and B1-B8 are locked together. The distance between the moving plate 10 and solenoid ring 14 closes step by step in a balanced fashion as previously described as each solenoid locks to its complementary permanent magnet. Blood is ejected out of the right ventricle 15 and left ventricle 16 via pulmonic valve 17 and aortic valve 18 respectively.

After a brief and predetermined interval, the blood from ventricles 15, 16 having been ejected into the pulmonary artery 61 or aorta 60 and retrograde flow being checked by the pulmonic 17 and aortic 18 valves respectively, each solenoid A1-A8 and B1-B8 will start to remove its hold on its corresponding rod 12. This can be accomplished by applying a current pulse, e.g., simultaneously to solenoid pairs B8 and A8, of opposite polarity and to the remaining solenoid pairs, stepwise and in reverse order. As each solenoid pair releases its lock on corresponding magnet 12 it pushes the plate 10 cranially step by step, in a balanced fashion. The spring force and systolic pressure force maintain the plate 10 in a cranial orientation during diastole.

FIG. 9A is a schematic side view of the helical springs 13, 26 forming a double helix as previously described in a fully uncompressed configuration, having longitudinal dimension X2. Not all magnetic rods 12 or 12' are illustrated for simplicity. FIG. 9B illustrates the springs 13, 26 of FIG. 9A in a fully compressed configuration, with magnetic rods 12, 12' locked down to their respective solenoids 14, and the spring 13 having longitudinal direction X1. In some embodiments, uncompressed dimension X2 is at least about 2×, 3×, 4×, 5×, 6×, 7×, 8×, 10×, or more with respect to the compressed dimension X1. FIG. 9C is a top view illustrating a plurality of solenoids A1-A8 and B1-B8 within solenoid ring 14.

FIG. 10A-10B schematically illustrate a close-up view of a helical spring 13 according to some embodiments of the invention. As illustrated, the spring 13 can have a first thicker portion 80 and a second thinner portion 81, portions 80, 81 made out of two distinct pieces of either the same or a different material, such as a metal or a polymer for example. The first thicker portion 80 could have a thickness in some embodiments that is at least 1.5×, 2×, 3×, 4×, 5×, 6×, 7×, 8×, 9×, 10×, 12×, 15×, as thick as the second thinner portion 81. The spring 13 can be divided into a number of segments 84, 85 divided at part line 82, such as 16 segments in some cases. The spring segments are formed from the thicker 80 of the two pieces of material using, for example, laser cutting, leaving negligible kerf removal. The spring 13 can also include a cavity 83, such as a "quarter circle" cavity removed from their upper corners, leaving only the thinner portion 81 to bend and deflect at joint 86. After attachment to the thin member 81 of the non-linear spring assembly 13, these quarter round cavities 83 now appear to be semicircles with the remaining thickness of the segments 84, 85 touching one another at line 82 as in FIG. 10B unless an adjacent segment 85 is forced up, as illustrated in FIG. 10A. Now the non-linear nature of the spring assembly is revealed, as best shown in FIG. 10A. In the deflected configuration shown in FIG. 10A, when one segment 85 of the spring 13 is forced upwards, only the thin portion 81 of the spring 13 moves and relatively little force is required. In the nondeflected configuration shown in FIG. 10B, showing the stiff or "hard" spring constant mode, if the left-hand side of the spring is constrained, it will take a large force on the right side of the assembly to deflect or bend the spring down.

FIG. 11 illustrates several consecutive segments of the non-linear spring 13 illustrated in FIGS. 10A-10B. As illustrated, spring 13 is connected to magnetic rods 12A1, 12A2. Magnetic rod 12A1 and the corresponding spring segment 84 is illustrated locked down to solenoid 14A1, after the solenoid 14A1 has pulled down its corresponding permanent magnet 12A1 by the small angle $\Phi$, while the adjacent solenoid 14A2 is positioned to attract the next spring segment 85 by the same angle $\Phi$ and longitudinal distance D11. In some embodiments, it is also possible for both solenoids 14A1 and 14A2 to be energized simultaneously. When a magnetic rod 12 exerts a force on a corresponding segment, the only spring assembly resistance comes from the bending of the thin member 81 of the spring assembly 13. The flexing of this thin portion 81 of the spring assembly 13 over the small angle $\Phi$ is one of only two mechanical sources of friction in the artificial heart, the second being the flexible walls, e.g., bellows. In some embodiments, the angle $\Phi$ is less than about 10 degrees, 5 degrees, 4 degrees, 3 degrees, 2.5 degrees, 2 degrees, 1.5 degrees, 1 degree or less, or between about 1.5 degrees and 2.5 degrees, or about 1.84 degrees. In some embodiments, the longitudinal distance D11 between a segment 84 locked to the corresponding solenoid 14A1 and an adjacent unlocked segment is between about 0.05-0.5 inches, such as between about 0.1 inches and about 0.3 inches, between about 0.1 inches and about 0.2 inches, or about 0.125 inches in some embodiments. Careful design allows long life and no fatigue failures since stresses can be readily held within the elastic limits of the metal used. When the left segment 84 is restrained and force is applied to the top of the adjacent segment 85 the "hard" spring constant of the spring assembly is revealed. The entire spring assembly 13 is available to resist the applied force and deflection of the assembly 13 is negligible to the forces generated by this artificial heart's solenoids 14A1, 14A2.

Parqueted and pre-finished hard wood floors is an analogy to the aforementioned spring concept. The factory made wood segments of parqueted floors are glued to a coarse but thin textile which keeps the often tiny wood segments firmly in place while providing a suitable surface for the flooring adhesive to bond to. Furthermore, similar to the spring segments shown in the configuration of FIG. 10B on a level surface the "hard" spring analogy prevents gaps from appearing on the surface of the installed floor. This technique permits rapid and precise installation of multi and small segmented hardwood floors.

FIGS. 12A and 12B illustrate a top view and side view, respectively of a non-linear helical spring 13 as previously described, with coupled magnetic rods 12. As illustrated in FIG. 12B, magnetic rods 12 may be housed therethrough within apertures 89 of the spring 13. Other apertures 88 are present to receive magnets 12 therethrough from other segments of the spring 13, to allow the spring 13 to advantageously assume a more fully compressed configuration.

Figure 13:
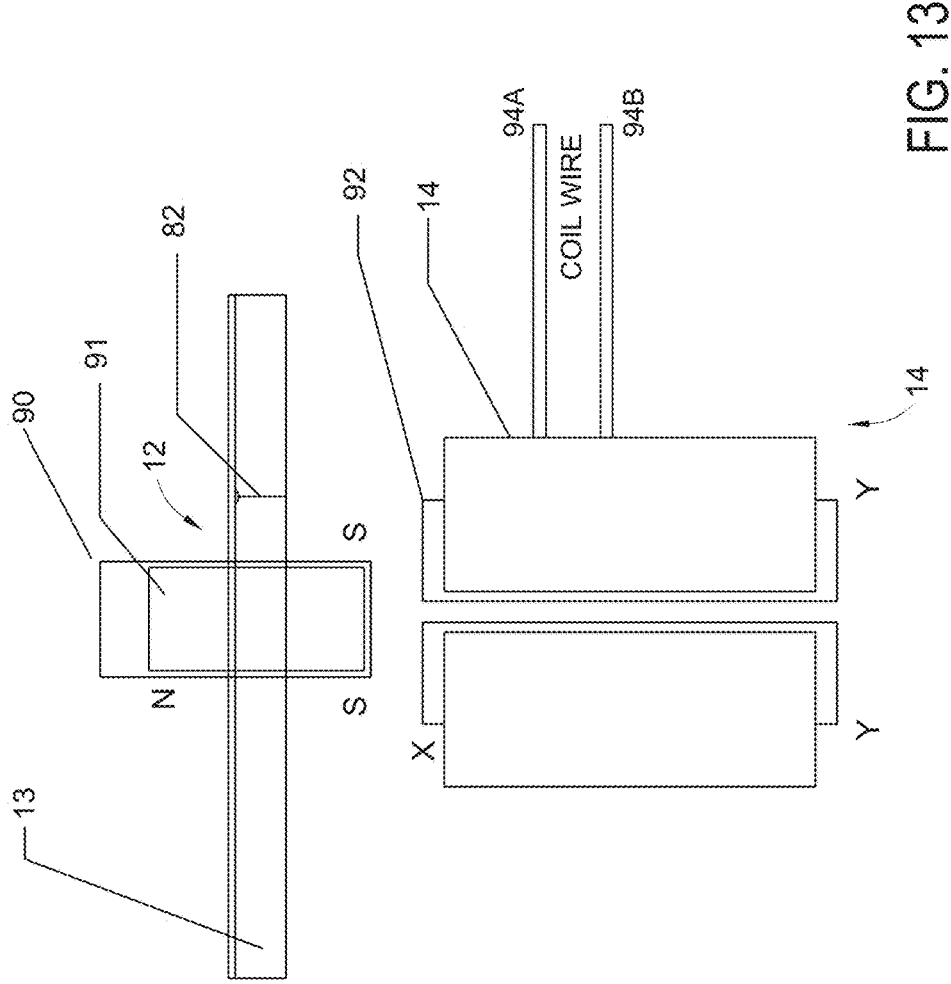
FIG. 13 illustrates more details of the manner in which the solenoid attracts the magnet of the spring.

FIG. 13 illustrates more details of the manner in which the solenoid 14 attracts the magnet 12 of spring 13. The spring magnets 12 and the solenoids 14 of the artificial heart comprise at least one magnetic material. The magnetic materials are placed in a generally magnetically aligned relationship as described elsewhere herein, to magnetically interact and actuate the axially movable plate 10 to facilitate the flow of blood into and out of the artificial heart.

In some embodiments, the spring magnets 12 and/or the solenoids 14 comprise a "hard" ferromagnetic material, which is also commonly referred to as a permanent magnet. A permanent magnet is characterized as a material showing resistance to external demagnetizing forces once being magnetized. That is, a high external magnetic field is required in order to remove the residual magnetism of a permanent magnet. Stated differently, a permanent magnet has very high intrinsic coercivity, which is a measure of its resistance to demagnetization. A permanent magnet possesses poles of opposite polarity. The poles are regions of a magnet (usually at the end of the magnets) where the external magnetic field is strongest. Relative to Earth's magnetic poles, if the magnet is free to turn, one pole will point to the magnetic north pole of the Earth, and is thus called a north pole of the magnet, which is indicated by N in the drawings or otherwise called an N-pole. The opposite pole is called a south pole of the magnet, which is indicated by S in the drawings or otherwise called a S-pole.

According to physical laws, poles of like polarity (N-N or S-S) repel each other with a magnetic force. Conversely, poles of unlike polarity (N-S or S-N) attract each other with a magnetic force. Thus, structures incorporating permanent magnets will repel each other when like poles of the structures are oriented to face each other, and likewise attract each other when opposite poles of the structures are oriented to face each other. The magnitude of the force of magnetic attraction or repulsion depends on the strength of the magnets and the distance between the poles.

Examples of known permanent magnet materials include alloys of Neodymium-Iron-Boron (NdFeB), alloys of Aluminum-Nickel-Cobalt (AlNiCo), and Samarium Cobalt (SmCo). An electromagnet (current flowing through a coil of wire) can be substituted for a permanent magnet; in certain embodiments the solenoid 14 comprises a relatively weak permanent magnet 92 along with a relatively strong electromagnet facilitated by coil wires 94A, 94B.

While various magnets, such as the spring magnets 12 can be referred to herein as magnetic rods, it will be appreciated that the magnets can each be configured in various ways and take various shapes, e.g., cylindrical, square, rectangular, or other polygons. In addition to discrete magnets, in some embodiments, bonded permanent magnets may also be used. Bonded magnets can be flexible or rigid, and consist of powdered NdFeB, Ferrite or SmCo permanent magnet materials bonded in a flexible or rigid substrate of e.g., silicone, rubber, nitrile, polyethylene, epoxy, polyvinyl chloride, or nylon. The forming of the bonded magnet can be achieved by extrusion, compression molding, injection molding, calendaring, or printing. Bonded magnets enable unique flexible designs, and durable high tolerance shapes that are otherwise difficult to achieve.

In some embodiments, the magnetic cores 91 of magnets 12 can be desirably coated, plated, encapsulated, or deposited prior to placement with a selected protective material 90. The protective material 90 is selected to provide a corrosion resistant and biocompatible interface, and can also be desirably selected to form a durable interface, to provide longevity to the system component, and thereby provide resistance to structural fatigue and/or failure.

The protective material 90 can be selected among various types of materials known to provide the desired biocompatibility, resistance to corrosion, and durability. For example, the protective material 90 can comprise titanium or ferrous material plated, deposited, or otherwise coated upon the magnetic material 91. As another example, the protective material 90 can comprise a parylene coating. As other examples, the protective material 90 can comprise a silicone polymer, a non-toxic epoxy, a medical grade polyurethane, or a U.V. curable medical acrylic co-polymer. The protective material 90 may be made up of various layers, each contributing to the protective and/or biocompatibility characteristics of the protective material.

In some embodiments, the magnet 12 has a brittle neodymium core 91 protected by a thin ferrous magnetic enclosure 90. Once in contact with the solenoid assembly 14 (e.g., by virtue of permanent magnetic core 92 of the solenoid 14), the magnet 12 of the spring 13 retains its position locked to the solenoid after power is removed from the solenoid coil 14. Solenoid coil 14 is operably connected to coil wires 94A, 94B. When a first polarity voltage, e.g., a positive voltage is applied to wire 94A and a second opposing polarity voltage, e.g., a negative voltage is applied to wire 94B, end X of the solenoid 14 will represent magnetic north and end Y of the solenoid 14 will represent magnetic south. The magnet 12 and corresponding segment of the spring 13 will then be positioned such that it is magnetically attracted to the solenoid 14, and then reversibly locked via action of the magnetic core 92 (e.g., a permanent magnetic core) of the solenoid, and in turn moving the operably connected movable plate 10 closer to the solenoid 14.

In a later sequence, the current pulse to the solenoid 14 is applied in opposite polarity, causing the permanent magnet to be repelled and separated from the solenoid. For example, when the second opposing polarity voltage, e.g., a negative voltage is applied to wire 94A and the first voltage, e.g., a positive voltage is applied to wire 94A, end X of solenoid 14 will be magnetic south while end Y of solenoid will be magnetic north, and the magnet 12 of the spring 13 will overcome the magnetic attractive force of the magnetic core 92 of the solenoid 14, and be repelled away from the solenoid 14, moving the moveable plate 10 further away from the solenoid 14.

FIGS. 14A-14D illustrate another embodiment of an artificial heart 95. Artificial heart 95 is similar to artificial hearts 50, 70 having various components as illustrated in FIGS. 4A-4B and FIGS. 7A-7B, some differences as illustrated in FIG. 14A being that spring assemblies are positioned near both the cranial and caudal ends of the artificial heart 95, and the solenoid assembly is positioned longitudinally therebetween, or in other words sandwiched in the middle of the two spring assemblies. Embodiments that include such a feature can advantageously allow for push and pull strokes making the solenoid operation more powerful and efficient. As noted with respect to other embodiments, the artificial heart 95 includes an outer housing 5.

Outer housing 5 includes one or more sidewalls 51, as well as top plate 3 and bottom plate 19. However, unlike the embodiments illustrated and described in connection with FIGS. 4A-4B and 7A-7B, central plate 10 is fixed, while top plate 3 and/or bottom plate 19 are movable along a generally longitudinally axis of the artificial heart 95, e.g., a cranial-caudal axis. The artificial heart could include a single spring on either side of the solenoid ring 14, a single spring on a first side and a plurality of springs on a second side of the solenoid ring 14, or a plurality of springs on both sides of the solenoid ring 14, such as a pair of springs in double helix configurations as previously described.

FIG. 14A also illustrates atrial springs 13, 29 configured as a double helix. First atrial spring 13 is operably connected at a first, e.g., cranial end via attachment point 27 to an atrial-facing surface of the top plate 3, and operably connected at second, e.g., caudal end via attachment point 25 to an atrial-facing surface of the solenoid ring 14. Second atrial spring 29 is operably connected at a first, e.g., cranial end via attachment point 26 to an atrial-facing surface of the top plate 3, and operably connected at second, e.g., caudal end via attachment point 11 to an atrial-facing surface of the solenoid ring 14. A plurality of magnets 12 are operably attached to atrial springs 13, 29 in a 1:1 or other ratio as previously discussed, the total number of magnets 12 corresponding in a 1:1 or other ratio to the number of solenoids within the solenoid ring 14.

Still referring to FIG. 14A, ventricular springs 31, 32 are also configured as a double helix. First ventricular spring 31 is operably connected at a first, e.g., cranial end via attachment point 33 to a ventricular-facing surface of the solenoid ring 14, and operably connected at second, e.g., caudal end via attachment point 20 to a ventricular-facing surface of the solenoid ring 14. Second ventricular spring 32 is operably connected at a first, e.g., cranial end via attachment point 34 to a ventricular-facing surface of the solenoid ring 14, and operably connected at second, e.g., caudal end via attachment point 30 to a ventricular-facing surface of the solenoid ring 14. A plurality of magnets 35 are operably attached to ventricular springs 31, 32 in a 1:1 or other ratio as previously discussed, the total number of magnets 35 corresponding in a 1:1 or other ratio to the number of solenoids within the solenoid ring 14. In the embodiment shown, there are a total of 16 magnets attached to atrial springs 13, 29, a total of 16 magnets attached to ventricular springs 31, 32, and a total of 16 corresponding solenoids 14, although other numbers as previously discussed can also be used depending on the desired clinical result.

FIG. 14B is a cross-sectional view through line B-B of FIG. 14A looking from a generally cranial to a generally caudal direction. The solenoid ring 14 (housed radially in between sidewall 51 of outer housing 50 and outer atrial wall 21 and/or ventricular wall 23) contains a plurality of solenoids, such as 16 solenoids as shown. However, other embodiments could include, for example, between about 2-64 solenoids, 4-32 solenoids, or 8-24 solenoids for example. These solenoids are marked 1A through 8A and 1B through 8B as illustrated. As noted previously, the first atrial spring 13 is connected at a caudal end to the atrial-facing surface of the solenoid ring 14 at position 25 and the second atrial spring 29 is connected at a caudal end to the atrial-facing surface of the solenoid ring 14 at position 11. Also illustrated are solenoid coils 28 as part of solenoid ring 14 within outer chamber 4, right atrium 6, left atrium 7, tricuspid valve 8, mitral valve 9, atrial septal wall 22 and atrial outer wall 21.

FIG. 14C is a top view through line A-A of FIG. 14A looking from a generally cranial to a generally caudal direction. Shown are an external surface of top plate 3, attachment points (in phantom) 26 and 27 of respective atrial springs 29 and 13, and openings within the top plate 3 for ingress of blood into the artificial heart 95 from the superior vena cava 1 and pulmonary vein 2. Inferior vena caval opening is not shown, and could be on the top plate 3, bottom plate 19, or sidewall 51. Alternatively, in some embodiments the superior vena cava could be anastomosed or otherwise attached to the inferior vena cava external to the artificial heart 95 creating a common return conduit for deoxygenated blood directly into the artificial heart 95.

With the axially moveable top wall 3 and bottom wall 19 of the artificial heart 95, in some embodiments it may be advantageous to anastomose one or more native vessels serving as a vascular conduit into or out of the artificial heart 95 to a longitudinally flexible graft material having bellows or accordion-like properties that is in turn operably attached to the artificial heart 95, to reduce shear forces at the attachment site of the vessels to the artificial heart 95.

FIG. 14D is a bottom view through line C-C of FIG. 14A looking up from a generally caudal to cranial direction. Shown are an external surface of bottom plate 19, attachment points (in phantom) 20, 30 of respective ventricular springs 31, 32, and openings within the bottom plate 19 for egress of blood out of the artificial heart 95 across the aortic valve 18 and pulmonic valve 17 and into the aorta 60 and pulmonary artery 61 respectively.

FIGS. 15-16 are two-dimensional schematic incline plane representations of the actual three-dimensional atrial helical springs 13, 29 and ventricular helical springs 31, 32 and solenoid ring 14 as previously illustrated and described, at different points in the cardiac cycle. As noted previously, cranial end of the first atrial spring 13 is attached to axially movable top plate 3 at attachment point 27, while the caudal end of the first atrial spring 13 is attached to the solenoid ring plate 14 at attachment point 25. Cranial end of the second atrial spring 29 is attached to axially movable top plate 10 ant attachment point 26, while the caudal end of the second atrial spring 29 is attached to the solenoid ring plate 14 at attachment point 11. Each atrial spring 13, 29 is operably connected to a plurality of magnets (e.g., magnet rods 12 connected to first spring 13, and magnet rods 12' connected to second spring 29) spaced apart along the length of the springs 13, 26, each magnet 12, 12' corresponding to a particular solenoid 1A-8A or 1B-8B respectively, such as in a 1:1 ratio.

Also as noted previously, first ventricular spring 31 is operably connected at a first, e.g., cranial end via attachment point 33 to a ventricular-facing surface of the solenoid ring 14, and operably connected at second, e.g., caudal end via attachment point 20 to a ventricular-facing surface of the solenoid ring 14. Second ventricular spring 32 is operably connected at a first, e.g., cranial end via attachment point 34 to a ventricular-facing surface of the solenoid ring 14, and operably connected at second, e.g., caudal end via attachment point 30 to a ventricular-facing surface of the solenoid ring 14. A plurality of magnets 35 are operably attached to ventricular springs 31, 32 in a 1:1 or other ratio as previously discussed, the total number of magnets 35 corresponding in a 1:1 or other ratio to the number of solenoids within the solenoid ring 14. In some embodiments, the attachment points are spaced approximately 180 degrees apart along a circumference of a wall, plate, or other structure such that the force is properly balanced.

At the start of the cardiac cycle, solenoids A1 and B1 are energized simultaneously. This unlocks the solenoid magnets 12, 12' in the atrial helical springs 13, 29 and pushes the top plate 3 away from the solenoid ring 14, while pulling the magnets 35, 35' on the ventricular helical springs 31, 32 in to lock on the associated solenoid magnets of A1-A8, B1-B8. The distance between the solenoid assembly 14 and the top plate 3 thus increases step by step in a balanced and synchronized way. The power is then removed from the solenoids A1 and B1. The magnets 35, 35' on the ventricular side A1 and B1 are strong enough to hold in and lock into the solenoid 14, and the magnets in atrium helical spring are far enough away from the solenoid to not relock on the A1 and B1 solenoids. Power is than applied to the A2 and B2 solenoids, this action continues for all the solenoids one pair at a time. This forces the bottom plate 19 in a cranial direction, increasing the pressure in the ventricles 15 and 16 closing the tricuspid value 8 and mitral valve 9 and ejecting blood out through the pulmonary valve 17 and aortic valve 18. FIG. 15 illustrates the artificial heart at a point in the cardiac cycle following ventricular contraction.

After the ventricular contraction is completed, reverse power is applied to the solenoids starting on A8 and B8. This action will unlock the magnets 35, 35' in ventricle helical springs 31, 32 associated with A8 and B8 and then lock the magnets 12, 12' in atrium helical springs 13, 29 associated with A8 and B8, pushing the bottom plate 19 axially away from solenoid coil assembly 14 and pulling the top plate 3 caudally toward the solenoid assembly 14. The power is then removed from the solenoids A8 and B8. The magnets 12, 12' on the atrial side A1 and B1 are strong enough to hold in lock and the magnets 35, 35' in the ventricular helical spring 31, 32 are far enough away from the solenoid to not relock on the A8, and B8 coils. Power is than applied to A7 and B7; these actions continue for all the solenoids one pair at a time. This forces the bottom plate 19 in a caudal direction, reduces the pressure in the ventricles 15 and 16 opens the tricuspid value 8 and mitral valve 9, thus allowing blood through to ventricles 15 and 16 and close the pulmonary valve 17 and aortic valve 18. This completes the cardiac cycle, and the heart system then awaits the next cycle.

FIG. 17 illustrates more details of a "push-pull" solenoid assembly similar to that of FIG. 13, with features as described in connection with FIGS. 14A-16 above. Single atrial and ventricular springs are illustrated for simplicity. Once in contact with the solenoid assembly 14 (e.g., by virtue of permanent magnetic core 92 of the solenoid 14), the magnet 12 of an atrial spring 13 retains its position locked to the solenoid after power is removed from the solenoid coil 14. Solenoid coil 14 is operably connected to coil wires 94A, 94B. When a first polarity voltage, e.g., a positive voltage is applied to wire 94A and a second opposing polarity voltage, e.g., a negative voltage is applied to wire 94B, end X of the solenoid 14 will represent magnetic north and end Y of the solenoid 14 will represent magnetic south. The atrial spring magnet 12 and corresponding segment of the atrial spring 13 will then be positioned such that it is magnetically attracted to the solenoid 14, and then reversibly locked via action of the magnetic core 92 (e.g., a permanent magnetic core) of the solenoid, moving the top plate 3 closer to the solenoid 14. Conversely, the ventricular spring magnet 35 facing the opposite pole of the solenoid 14, will be positioned such that it is repelled from the solenoid 14, moving the bottom plate 19 away from the solenoid 14.

In a later sequence, the current pulse to the solenoid 14 is applied in opposite polarity, causing the atrial spring magnet 12 to be repelled and separated from the solenoid 14. For example, when the second opposing polarity voltage, e.g., a negative voltage is applied to wire 94A and the first voltage, e.g., a positive voltage is applied to wire 94A, end X of solenoid 14 will be magnetic south while end Y of solenoid 14 will be magnetic north, and the magnet 12 of the atrial spring 13 will overcome the magnetic attractive force of the magnetic core 92 of the solenoid 14, and be repelled away from the solenoid 14, in turn moving the top plate 3 away from the solenoid 14. Conversely, the ventricular spring magnet 35 facing the opposite pole of the solenoid 14, will be positioned such that it is magnetically attracted to the solenoid 14, moving the bottom plate 19 closer toward the solenoid 14.

Disclosed herein are additional embodiments of an artificial heart. Some embodiments can be less than about 80%, 70%, 60%, 50%, 40%, 30%, or less in size (e.g., one, two, or more dimensions) than embodiments disclosed above. The heart can share a pumping mechanism for both ventricular chambers, and as such allows for a very compact size profile for the artificial heart. The heart valves can be sufficiently large to allow increased, less turbulent blood flow. In some embodiments, the cross-sectional area of one or more of the valves is at least about 10%, 15%, 20%, 25%, 30%, 35%, 40%, or more with respect to the cross-sectional area of the artificial heart 1800 at that given cross-section. The artificial heart can include a housing, a plurality of opposing bellows springs, and a movable magnet module operably attached to the bellows springs. In some embodiments, the bellows spring and the magnet module are the only moving parts of the entire artificial heart system.

Figures 18, 18A, 18B:
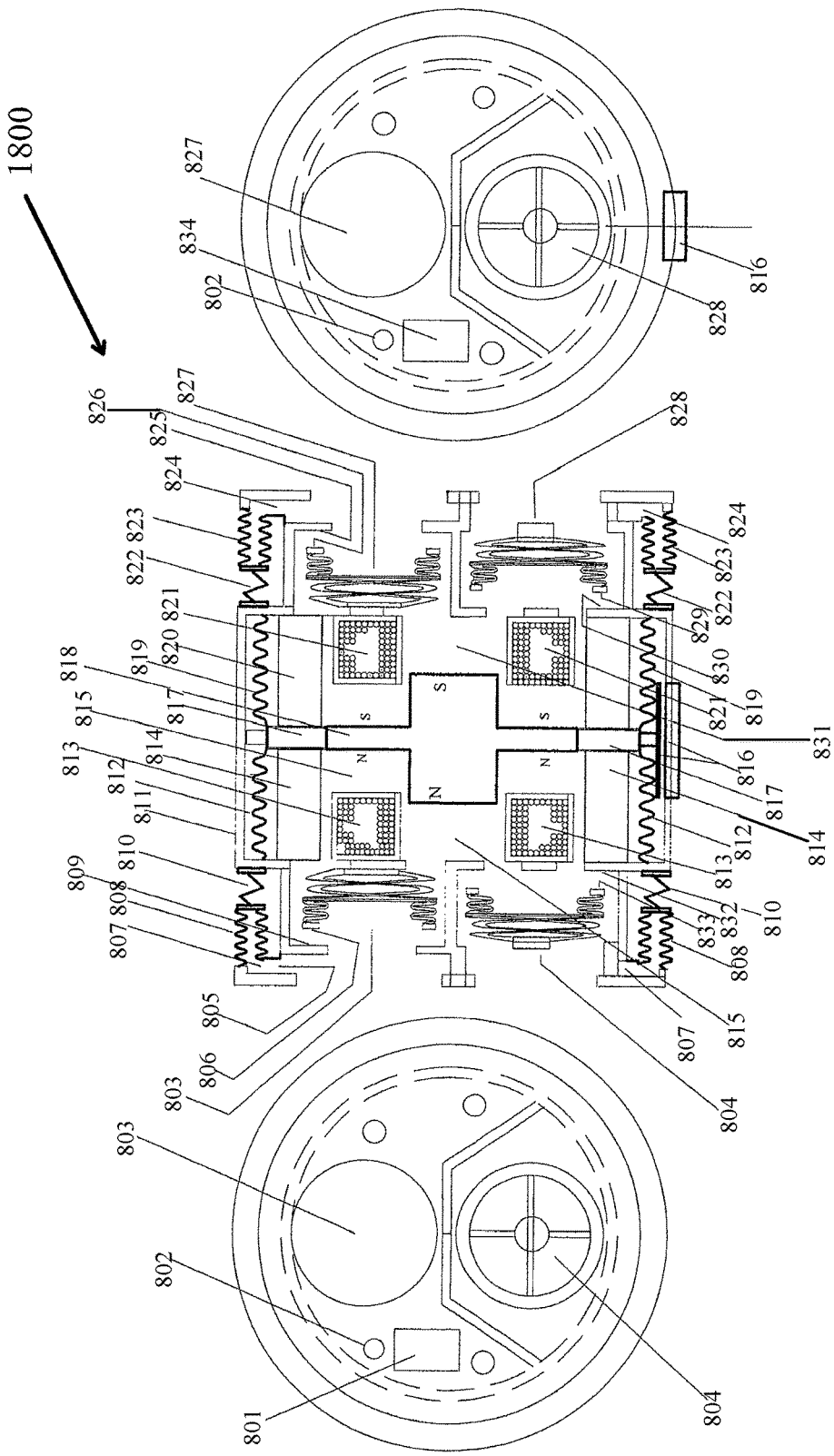
FIGS. 18-18B illustrates schematically an embodiment of a compact artificial heart having an axially movable central magnet.
FIG. 18AA illustrates a laser position sensor module, according to some embodiments of the invention.
Figure 18A:
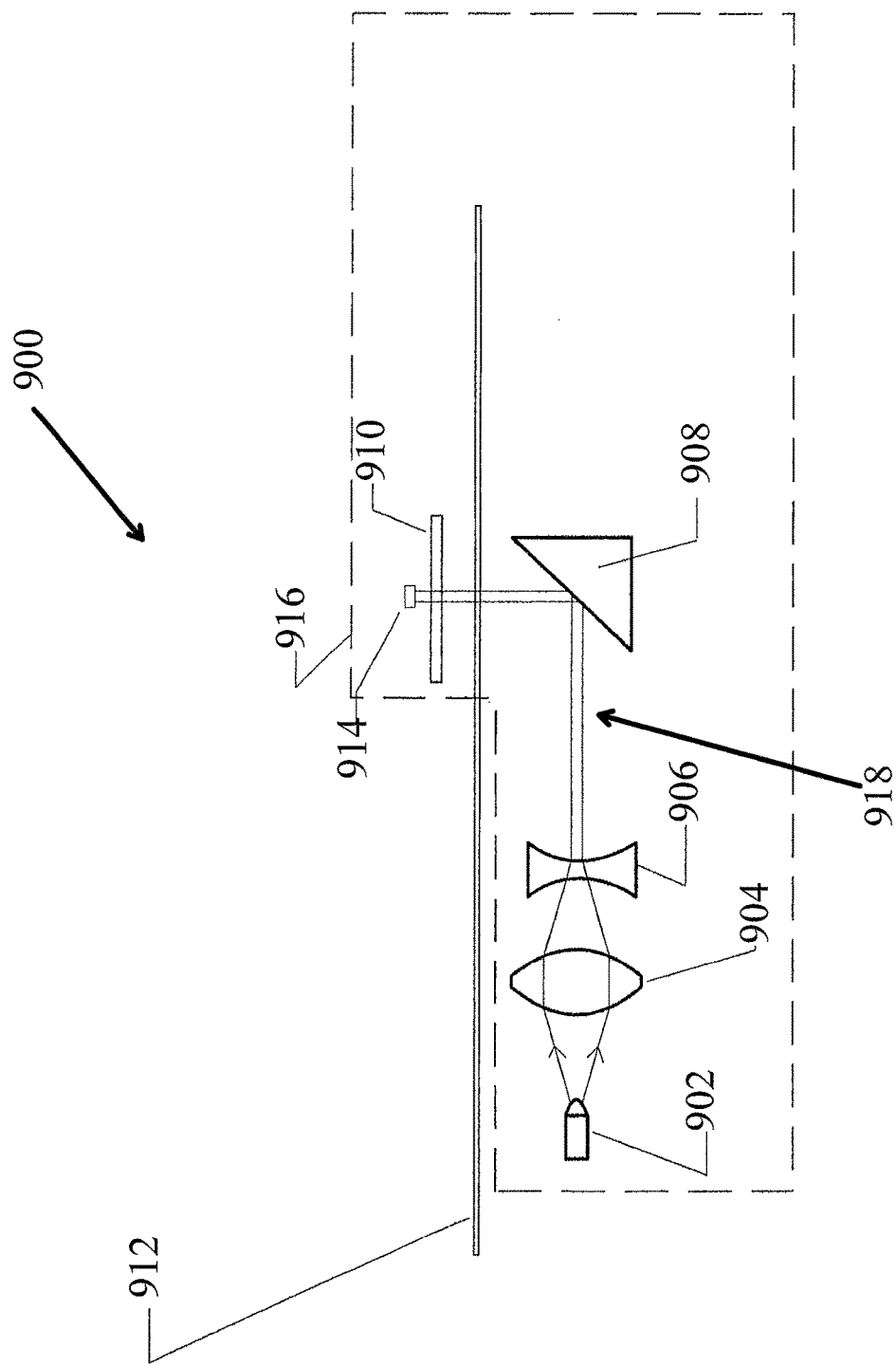

FIG. 18 illustrates an artificial heart 1800 according to some embodiments of the invention, including a plurality of chambers 806, 809 (e.g., a right ventricle 815, and a left ventricle 831) contained within a housing of any appropriate shape, such as a cylindrical structure 811 in some embodiments. Also shown in FIG. 18 are four valves 803, 804, 827, and 828 (e.g., tricuspid valve 803, pulmonic valve 804, mitral valve 827, and aortic valve 828). Vessels including the pulmonary vein, aorta, pulmonary artery, and vena cava are not illustrated for simplicity. In some embodiments, each of the artificial heart's valves can include a movable valve ring that reversibly contacts a fixed valve plate in order to create a valve seal. For example, the tricuspid valve 803 can include a movable tricuspid valve ring 806 that reversibly contacts the tricuspid valve plate 809. The pulmonic valve 804 can include a movable pulmonic valve ring 833 that reversibly contacts the pulmonic valve plate 832. The mitral valve 827 can include a movable mitral valve ring 826 that reversibly contacts the mitral valve plate 825. The aortic valve 828 can include a movable aortic valve ring 829 that reversibly contact the aortic valve plate 830. In some embodiments, one, two, or more of the valves can include helical springs operably connected to bellows springs, which are in turn operably attached to the moveable valve ring to advantageously facilitate gentle minimal force closure of the valve, as described in Applicant's co-pending U.S. patent application Ser. No. 14/603,101 entitled "Gentle Artificial Heart Valve with Improved Wear Characteristics" filed on Jan. 22, 2015, and hereby incorporated by reference in its entirety.

In some embodiments, the artificial heart 1800 has common right and left atrio-ventricular cavities. In some embodiments as illustrated in FIG. 18, the artificial heart 1800 can have discrete atrial chambers such as the right atrium 807 and left atrium 824, each having at least one movable wall operably connected to an atrial bellows spring 823, 808 operably connected to a respective atrial helical spring 822, 810. The atrium 807, 824 allow for continuous blood inflow with pressure control. Filling of the atrium 807, 824 with blood can cause movement of the atrial helical spring 822, 810 to increase intraatrial pressure and cause the respective tricuspid valve 803 and the mitral valve 827 to open, moving blood from the atria into the ventricles.

Still referring to FIG. 18, a magnet 818 can reside in a relatively central location of the artificial heart 1800, and be operably connected to movable heart plate structure 817, which can be configured to act as the cardiac "pump". The magnet 818 could include both substantially horizontal and vertical magnetic elements as illustrated in some embodiments, and north and south poles N, S as illustrated, and can be an electromagnet (or permanent magnet in other embodiments). The magnet 818 can be moved in a first direction or a second direction a predetermined distance opposite the first direction via opposing powered solenoids, or coils 813, 821. The magnet 818 can be operably connected on each side to right bellows 819 and left bellows 812 respectively, the bellows 819, 812 defining at least two respective chambers 815, 831. Each of the right bellows 819 and the left bellows 812 can include spring elements, and/or be each operably connected to one or more respective helical springs, e.g., right helical spring 814 and left helical spring 820 also configured to assist the magnet 818 to move at the start of heart motion and stop moving at the end of heart motion of each cardiac cycle. In some embodiments, the blood flow path can directly or indirectly contact the solenoids in order to cool the solenoids.

Also illustrated in FIG. 18 are fixed valve plates, including pulmonary valve plate 832 and aortic valve plate 830, which are operably connected to one of the ends of their respective bellows 819, 812. Further illustrated are one or more sensors, such as position and/or speed sensors 816 configured to determine the position, speed, and/or other parameters of the movable magnet 818 within the artificial heart 1800, described further below.

FIG. 18AA illustrates schematically an embodiment of a position sensing module 900 configured to detect the position or other parameters of the magnet within the artificial heart 1800 as previously described. In some embodiments, the module 900 can include a fixed, stationary component 916 that can be mounted to the housing of the artificial heart 1800, such as at the inner wall. The module 900, e.g., the stationary component 916 can include a laser 902 configured to project a laser beam 918 through focus lens 904, collimator 906, and then mirror 908, which allows the laser beam 918 to reflect at an angle, such as a right angle as shown. The laser beam 918 can then travel through position marker screen 910 to laser detector 914. The module 900 can also include a movable portion that includes a position marker plate 912 operably mounted to the magnet and configured to move along with the magnet 18. As such, the laser source 902 can initially project the laser beam 918 in a first direction, such as substantially parallel to the longitudinal axis of the position marker plate 912 in some embodiments, and the mirror 908 can reflect the laser beam 918 in a second direction. In some embodiments, the second direction is transverse to the longitudinal axis of the position marker plate 912 as shown. Such embodiments can be advantageous in some cases to ensure that the laser source 902 and the laser sensor 914 are in sufficient proximity to properly function.

FIGS. 18A and 18B schematically illustrate end views of the right heart and left heart respectively. FIG. 18A illustrates various artificial right heart structures including the tricuspid valve 803, pulmonic valve 804, a first control circuit 801 and hardware 802. FIG. 18B illustrates various artificial left heart structures including the mitral valve 827, aortic valve 828, a second control circuit 834, and hardware 802.

In some embodiments, a cardiac cycle of an embodiment of an artificial heart can be described as follows, and illustrated schematically in FIG. 19. At the start of the operation right coil 813 and left coil 821 are supplied power, and a servomechanism keeps magnet 818 in Position 1 as shown (and illustrated in greater detail in FIG. 19H), where the magnetic tracking force on the right coil 813 is equal or substantially equal to the combined force of the spring force of the bellows 819, 812 and/or the helical springs 820, 814; the artificial heart system 1800 is at rest. Prior to activation of the servomechanism system, the magnet power may control the position, and lock the magnet to one side or the other. Once the servomechanism is activated, the magnet 818 can move to a predetermined position. In some embodiments, the predetermined position in preset by the servomechanism software and/or hardware, and may be, for example, a minimum of about 0.10 inches, 0.05 inches, or 0.01 inches from the locked position. Since the servomechanism can include a phase lock system, the servomechanism position can be absolute depending on a servomechanism gain system. The position can be selected to avoid certain components directly touching each other when the servomechanism is active (except in some embodiments at the start when power is off). Temperature, manufacturing tolerances, and other variables can be taken into account to avoid servomechanism overshooting and other variables.

The heart cycle then begins as power is applied to coils 813, 821, to move the magnet in Direction 1 illustrated by the arrow. Right and left bellows springs 819, 812 as well as right and left helical springs 814, 820 respectively assist in providing a pushing or pulling force to move magnet 818 in Direction 1 with the force stored in the bellows springs 819, 812 and helical springs 814, 820. When the magnet 818 is moved in Direction 1, deoxygenated blood moves into right heart chamber 806 from the vena cava and oxygenated blood moves out of left heart chamber 809 into the aorta. As magnet 818 moves, its, speed, direction, and location can be sensed via one or more optical or non-optical sensors 816 configured to detect the speed, direction, and/or location of the magnet 808. The sensors 816 can be three-channel high-resolution sensors in some embodiments. The magnet 818 can move according to a predetermined profile set configured to preset the speed, direction of movement, and location of the magnet 818. The servomechanism (not shown) can be a high gain, phase lock, digital feedback system in some embodiments. The magnet 818 can move according to the pre-programmed speed stored, for example, in a memory and configured to position the magnet 808 within the heart 1800 within, for example, a tolerance of about 50 micrometers, or within about 0.01, 0.005, or 0.002 inches in some embodiments. The servomechanism controlling the electromagnetic forces, in combination with feedback from the sensors and/or customizing the spring constants of the helical springs, can be advantageously precisely configured such that various parts, do not physically contact each other even during systole or valve closure, preventing associated component wear. For example, the movable heart plate structure 817, when in use in some embodiments may not actually touch the surface of the corresponding aortic valve plate 830 or the pulmonary valve plate 832, but rather are in substantially close proximity to each other to effectuate functional valve closure. For example, two valve surfaces can rather come within, for example, within about 0.5, 0.4, 0.3, 0.2, 0.1, 0.09, 0.08, 0.07, 0.06, 0.05, 0.04, 0.03, 0.02, 0.01 inches, or less of each other, e.g., to close the valve without actually touching, which advantageously eliminates or substantially eliminates friction and component wear, and results in a very long operating life compared with conventional artificial hearts. Other embodiments as also disclosed herein can be configured such that no physical contact between valve surfaces occurs.

The forces supplied to magnet 818 to move in Direction 1 at the start are provided by coil 813, bellows springs 819, 812, and/or helical springs 814, 820. As the magnet moves to the center (e.g., Position 2, and illustrated in greater detail in FIG. 19B), the net force provided by bellows springs 819, 812 and helical springs 814, 820 are reduced to almost zero, e.g., equal in the opposite direction. The driving force provided by powered coils 813, 821 is also reduced as the efficiency of the driving force decreases as the magnet approaches Position 2. The kinetic energy within the magnet 818 keeps the magnet 818 moving past the midline of Position 2 in Direction 1 toward Position 3 (and illustrated in greater detail in FIG. 19C). As magnet 808 moves closer to Position 3, the bellows springs 819, 812, and/or helical springs 814, 820 start to slow down the movement of the magnet 818 and energy is stored in the bellows springs 819, 812, and/or helical springs 814, 820. Coil 821 supplies the most energy to move magnet 808 toward Position 3 as it becomes the most efficient at its proximity. When the magnet 818 reaches Position 3 (where the combined spring forces equal the magnetic attraction force), the sensors 813 will recognize the pre-programmed position, and the system will reverse the drive direction, moving magnet in Direction 2 opposite of Direction 1. Aortic valve 828 will be configured to close, and mitral valve 827 will open allowing the blood to enter the left heart chamber 809 and the blood in right heart chamber 806 is forced out through the pulmonary valve 804 into the pulmonary artery (not shown). The tricuspid valve 803 will then be configured to close. The operation of magnet 818 moving in Direction 2 follows the same pattern as described above, but in reverse, back toward Position 2 (and illustrated in greater detail in FIG. 19D). When sensor 816 senses that magnet 818 reaches Position 1, the servomechanism controller will hold the magnet 818 in Position 1 (concluding the heart cycle) until the next heart cycle begins. The servomechanism controller can have a preprogrammed heart rate, or respond to feedback from various internal or external inputs. The program can be stored in a memory. FIG. 19E illustrates sectional views of an artificial heart 1800 with magnet in center Position 2. FIG. 19F illustrates a cross-sectional view through line X-X in the direction of arrows. FIG. 19G illustrates a cross-sectional view through line Y-Y in the direction of arrows.

The power drives on the coils can be switching regulated high-voltage drive coils in some embodiments to increase efficiency. The power can be sufficient to drive the artificial heart when the magnet is in the center position. An oscillation motion in the coils provided in the controller program can allow the system to recover. In operation, kinetic energy stored in the magnet itself is sufficient to move the magnet in a desired direction through the center position without stopping. The operation of the coils can be pre-programmed to provide efficiency.

Figure 19:
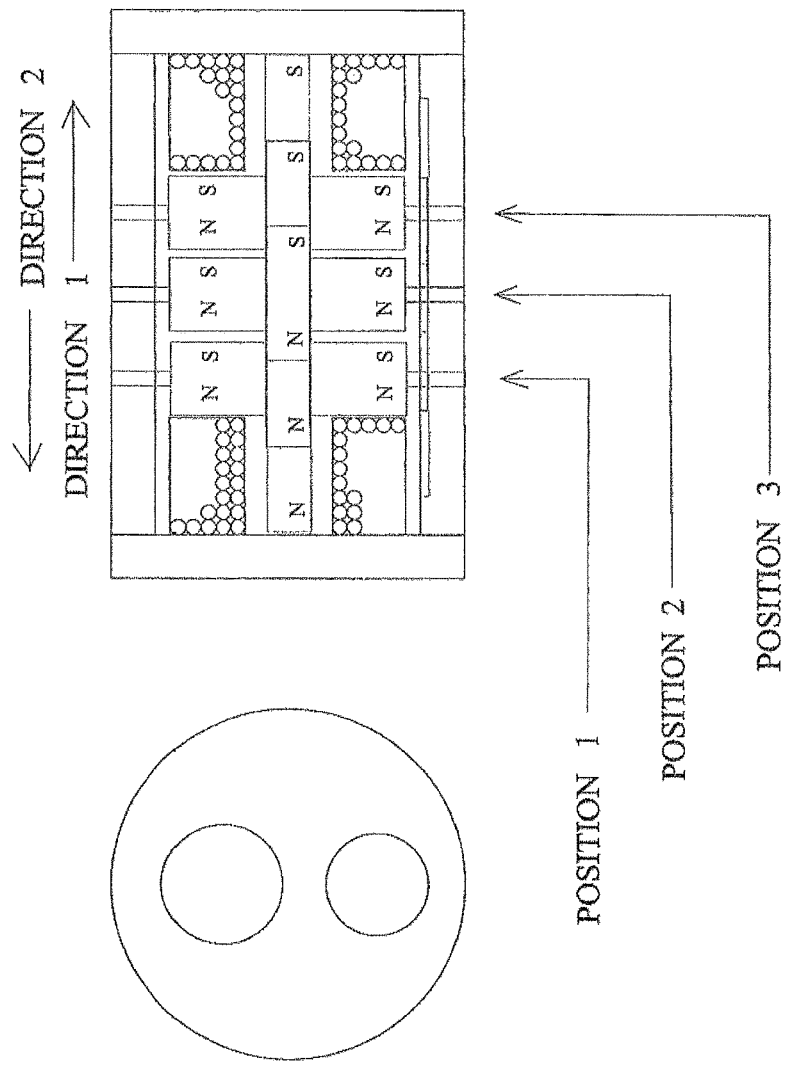
FIG. 19-19G illustrates schematically operation of the artificial heart of FIG. 18 with a moving magnet at various positions of operation.
Figure 19B:
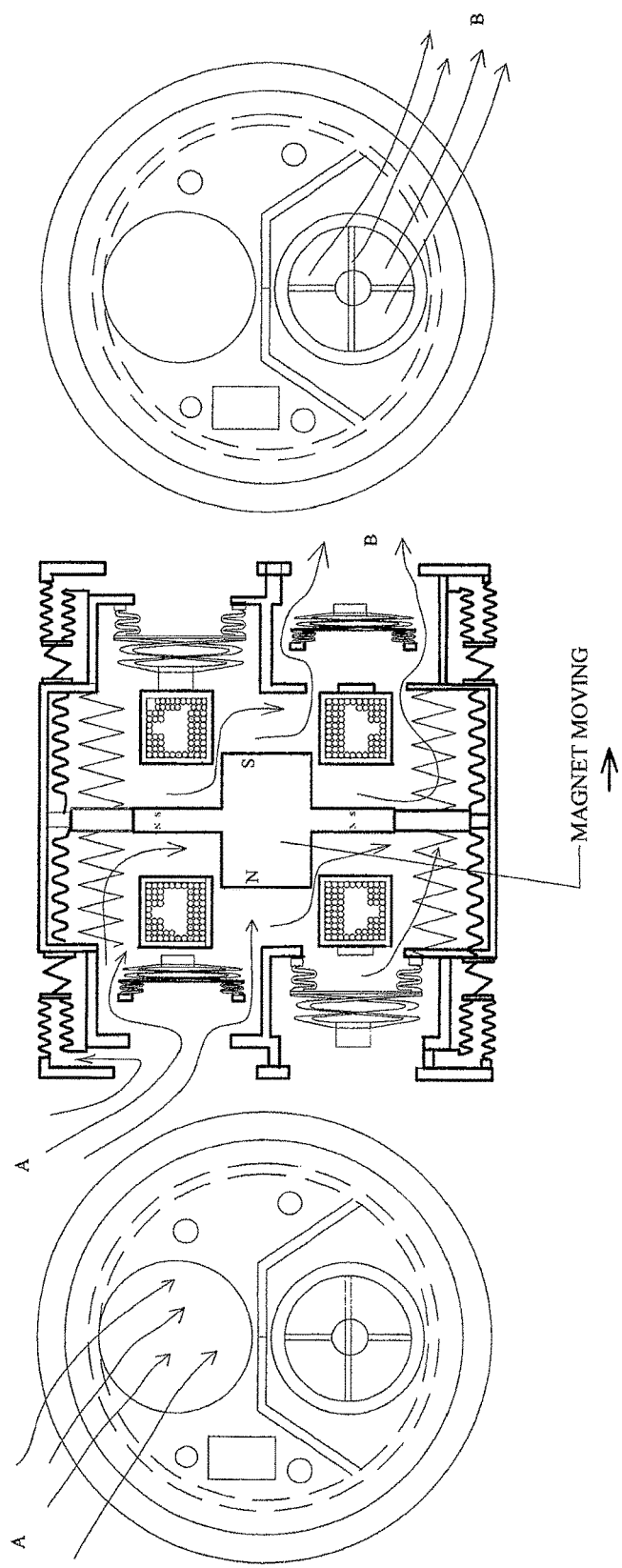
FIG. 19H illustrates a graphical relationship of magnet position with respect to the forces on the magnet, in accordance with some embodiments.
FIG. 19I illustrates an embodiment of functionality of a multi-channel location, direction, and speed sensor configured to be in operative communication with a controller.
Figure 19D:
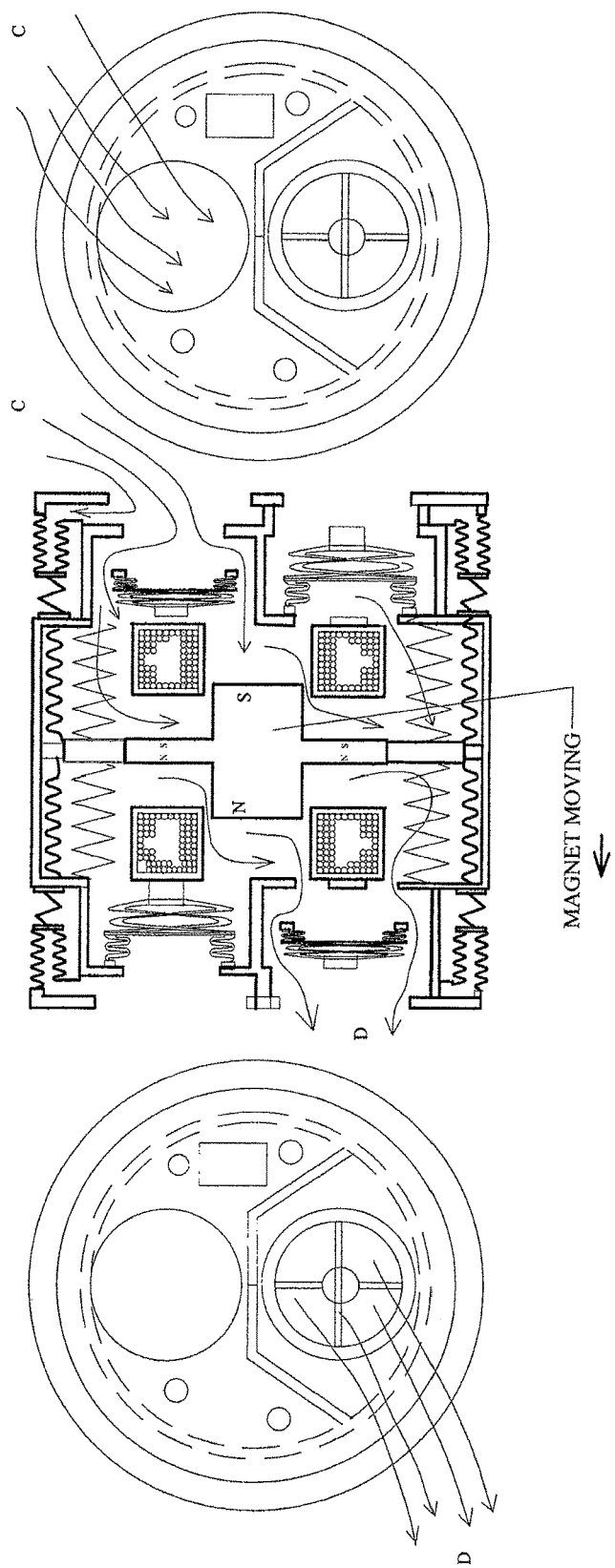
Figure 19E:
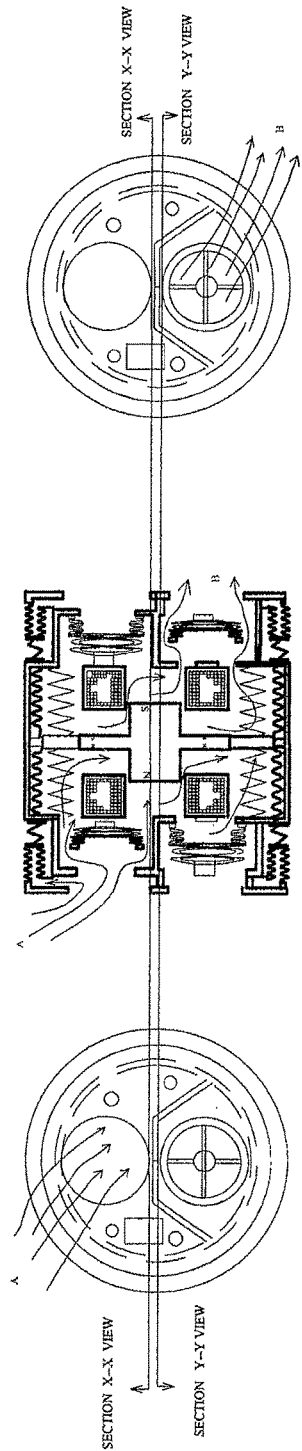
Figure 19F:
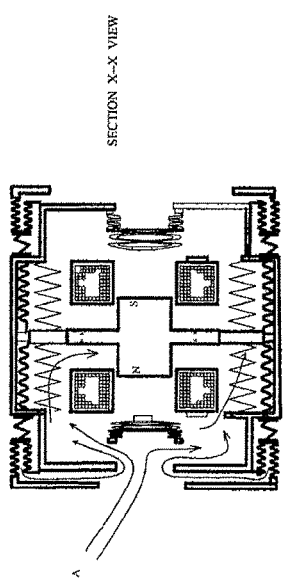
Figure 19G:
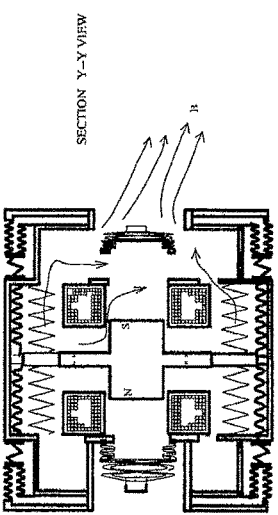
Figure 19H:
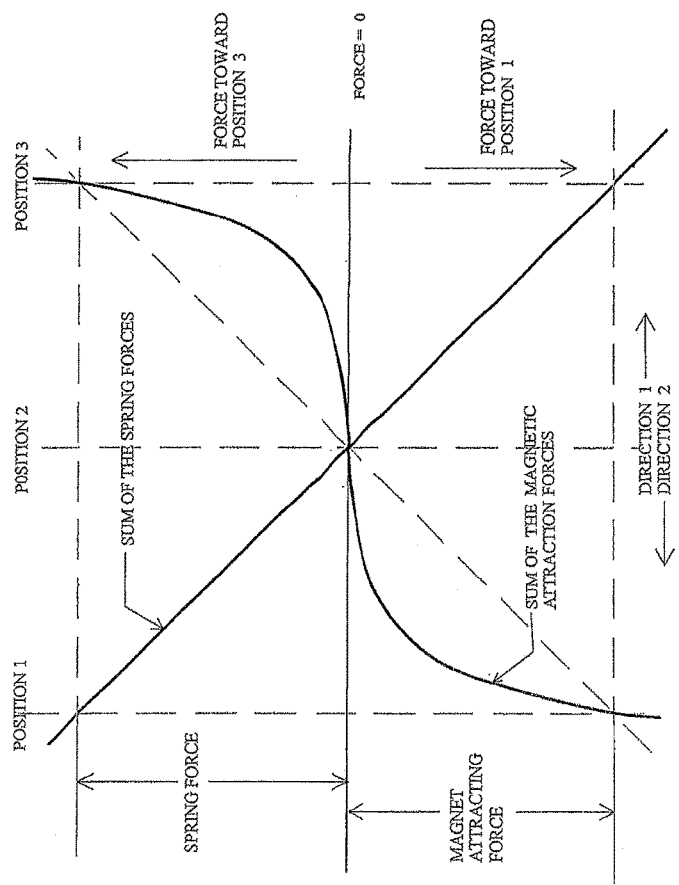

FIG. 19H is a graph illustrating magnetic position (as illustrated in FIG. 19) with respect to various forces on the magnet as the magnet travels bi-directionally toward Direction 1 and Direction 2 opposite Direction 1. As shown, at Position 1, the start of the heart cycle, the spring forces are equal to the magnetic attraction force. At Position 2, the central position of the magnet, the spring force and the magnetic attraction forces are both zero. At Position 3, the end of the magnet travel, the magnetic attraction force is equal to the spring force. As illustrated, the sum of the spring forces can be generally linear as shown, while the sum of the magnetic attraction forces can take the shape of two halves of parabolic curves as shown.

Figure 19I:
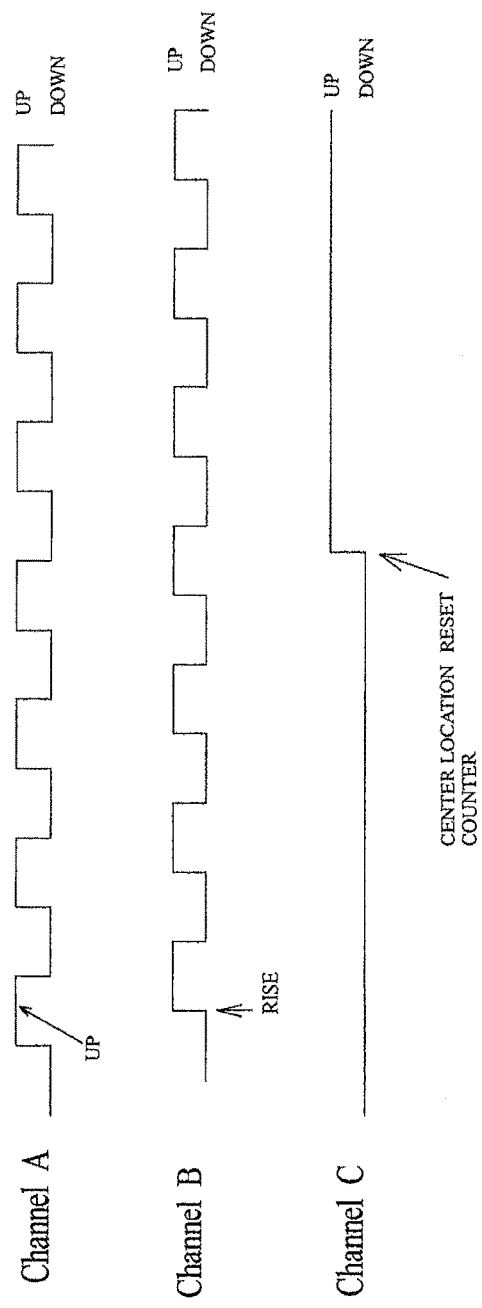

FIG. 19I illustrates an embodiment of functionality of a multi-channel location, direction, and speed sensor configured to be in operative communication with a controller, such as a 3 channel location, direction, and speed sensor. The sensor can optionally include a bidirectional counter, such as an up-down counter. In some embodiments, a control processor can be configured to amplify the sensor signal, and/or perform a counting function. As illustrated, each channel has first "up" states and second "down" states. As illustrated, Channel B rises as A is in the "up" state, as the magnet 18 moves toward Position 1, and the bidirectional counter is counting "up". Channel B rises as Channel A is in the "down" state, as the magnet moves toward Position 3, and the bidirectional counter is counting "down". The "up" and "down" counter is utilized to determine the location of the magnet 18. The rate or frequency of the count will translate into the speed of the moving magnet 18. Channel C changes at the center Position 2, in the location shown; and resets the bidirectional counter in the center position. If Channel C is in the "down" position, the magnet 818 is relatively closer to Position 1 than Position 3. If Channel C is in the "up" position, the magnet 818 is relatively closer to Position 3 than Position 1. In some embodiments, the controller can be configured to receive data from one or more physiologic sensors that can determine blood pressure, blood oxygen level, temperature, hemoglobin level, or other parameters from blood flowing through the artificial heart, and adjust operation of the heart to better optimize efficiency.

Figure 20:
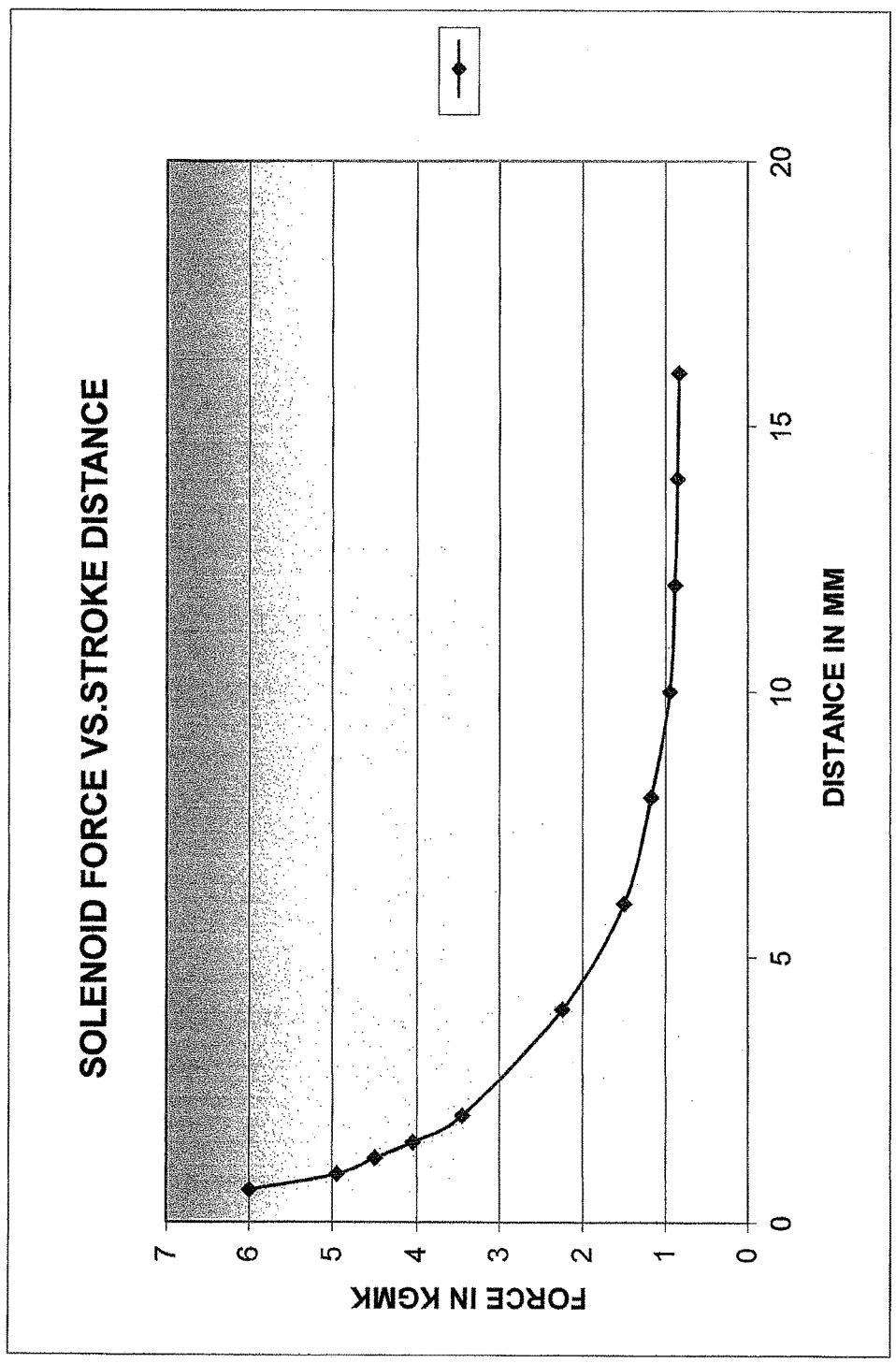
FIG. 20 illustrates a graphical relationship of solenoid force (in Newtons) on the Y axis with respect to stroke distance (measured in millimeters).

The bellows springs and/or helical springs can provide high efficiency in some embodiments. If a spring is compressed to a distance X with a force F, the energy stored in the spring E can be equal to the product of F and X. This stored energy can be released from the magnet with minimal loss regardless of the velocity of the traveling magnet, or the time of each cycle. The solenoids can be at their most efficient positions to convert electric energy when the coils are in close proximity to the moving magnet. FIG. 20 illustrates a graphical relationship of solenoid force (in Newtons) on the Y axis with respect to stroke distance (measured in millimeters) in an embodiment of an artificial heart 1800, according to some embodiments of the invention.

In some embodiments, the atrial volume and ventricular volume are shared within each respective chamber; atrial volume can increase, and ventricular volume can decrease in a 1:1 correlation to the atrial volume increase upon movement of the magnet in an appropriate direction, and vice versa. In some embodiments, the left and right heart pumping elements are also shared. However, in some embodiments the artificial heart 1800 can include discrete atria as illustrated. The heart and/or any of its components can be made, for example, of a biocompatible material, such as a metal, such as titanium or an alloy thereof, including SuperFlex titanium metal that has advantageous memory as well as an extended flexing range.

Various other modifications, adaptations, and alternative designs are of course possible in light of the above teachings. Therefore, it should be understood at this time that within the scope of the appended claims the invention may be practiced otherwise than as specifically described herein.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "attaching an artificial valve to a native valve annulus" includes "instructing the attaching of an artificial valve to a native valve annulus." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. An artificial heart, comprising:
    an outer housing comprising a right heart valve plate and a left heart valve plate spaced axially apart by a first bellows spring and a second bellows spring;
    a solenoid connected to a first drive coil and a second drive coil, the first drive coil operably connected to the right heart valve plate and the second drive coil operably connected to the left heart valve plate;
    a magnet operably connected to a plate structure spaced axially between the first drive coil and the second drive coil, the magnet operably connected to a first end of the first bellows spring and a first end of the second bellows spring, the magnet configured to move axially upon activation of the first drive coil and the second drive coil resulting in conversion of electrical energy to mechanical energy, thereby axially elongating one of the first bellows spring and the second bellows spring and simultaneously contracting the other of the first bellows spring and the second bellows spring resulting in the release of energy, moving blood in or out of the artificial heart by movement of the plate structure;
    at least one sensor configured to determine at least one of the position, velocity, and direction of travel of the magnet; and
    a servomechanism controller configured to receive data from the sensor and control power to the first drive coil and the second drive coil, thereby actuating the magnet and the plate structure.

2. The artificial heart of claim 1, wherein the servomechanism controller is configured to provide precise control of a position and speed of the magnet at all times.

3. The artificial heart of claim 1, wherein the solenoid is configured to actuate the magnet.

4. The artificial heart of claim 1, wherein the artificial heart comprises biocompatible titanium.

5. The artificial heart of claim 1, wherein the outer housing is rigid.

6. The artificial heart of claim 1, wherein the controller comprises a high gain, phase lock digital servomechanism feedback system.

7. The artificial heart of claim 1, wherein the controller is configured such that the plate structure never physically touches the left heart valve plate or the right heart valve plate during normal operation, thus increasing operating life.

8. The artificial heart of claim 7, wherein the controller is configured to receive data from the at least one sensor regarding at least one of blood pressure, blood oxygen level, and blood temperature, analyze the data, and adjust power to the first drive coil and the second drive coil accordingly.

9. The artificial heart of claim 1, wherein the artificial heart is configured such that the plate structure can move to within about 0.01 inches of the left heart valve plate or the right heart valve plate without actually contacting the left heart valve plate or the right heart valve plate during normal operation.

10. The artificial heart of claim 1, wherein the outer housing comprises discrete left and right atrial chambers.

11. The artificial heart of claim 10, wherein the discrete left and right atrial chambers are configured to control pressure and range of operation.

12. The artificial heart of claim 1, wherein the artificial heart is configured such that blood flow through the artificial heart directly cools the solenoid.

13. The artificial heart of claim 1, wherein the at least one sensor is configured to determine at least one of blood pressure, blood oxygen level, and blood temperature.

14. The artificial heart of claim 1, wherein each of the first and second drive coils, right and left heart valve plates, and at least one sensor are parts mounted to the artificial heart, wherein the artificial heart does not comprises any loose wires or sensors, and wherein the artificial heart is configured to minimize force on the parts when the artificial heart is pumping.

* * * * *